(12) United States Patent
Sugiyama et al.

(10) Patent No.: US 8,187,169 B2
(45) Date of Patent: May 29, 2012

(54) MEDICAL APPARATUS

(75) Inventors: Yuta Sugiyama, Hachioji (JP);
Kazuhiko Takahashi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 657 days.

(21) Appl. No.: 12/257,924

(22) Filed: Oct. 24, 2008

(65) Prior Publication Data
US 2009/0112060 A1 Apr. 30, 2009

(30) Foreign Application Priority Data
Oct. 25, 2007 (JP) ................................ 2007-277901

(51) Int. Cl.
*A61B 1/00* (2006.01)
(52) U.S. Cl. ..................... 600/106; 600/104; 600/118
(58) Field of Classification Search .................. 600/104, 600/106, 107, 114, 118, 145–146, 153; 604/95.01–95.05
See application file for complete search history.

(56) References Cited

U.S. PATENT DOCUMENTS

| | | | | |
|---|---|---|---|---|
| 2007/0185377 A1* | 8/2007 | Murakami et al. | ............ | 600/106 |
| 2007/0239106 A1* | 10/2007 | Weitzner et al. | ............ | 604/95.01 |

FOREIGN PATENT DOCUMENTS

| | | |
|---|---|---|
| EP | 1 782 744 A2 | 5/2007 |
| EP | 1 815 810 A1 | 8/2007 |
| JP | 06-209999 A | 8/1994 |
| JP | 06-285009 A | 10/1994 |
| JP | 07-000350 | 1/1995 |
| JP | 07-059730 | 3/1995 |
| JP | 08-224241 | 9/1996 |
| JP | 2002-238844 A | 8/2002 |
| JP | 2003-339632 | 12/2003 |
| JP | 2004-180830 | 7/2004 |
| WO | WO 2006/106881 A1 | 10/2006 |

OTHER PUBLICATIONS

Extended European Search Report dated Mar. 29, 2010.

* cited by examiner

*Primary Examiner* — Matthew J Kasztejna
*Assistant Examiner* — Ryan Henderson
(74) *Attorney, Agent, or Firm* — Scully, Scott, Murphy & Presser, P.C.

(57) ABSTRACT

A medical apparatus includes a first medical device, a second medical device, an integrated inputting device, and an integrated control device. The first medical device includes an insertion portion having a bending portion that is bent by a first driving portion and a first control device controlling the first driving portion. The second medical device includes an external force applying portion applying an external force to the insertion portion, a second driving portion allowing the external force applying portion to be operated, and a second control device controlling the second driving portion. The integrated inputting device instructs a distal end of the insertion portion to be moved to a target position or a target posture or in a target direction. Integrated control device controls at least one of the first driving portion and the second driving portion on the basis of an instruction from the integrated inputting device.

8 Claims, 19 Drawing Sheets

MEDICAL APPARATUS

This application claims benefit of Japanese Application No. 2007-277901 filed in Japan on Oct. 25, 2007, the contents of which are incorporated by this reference.

BACKGROUND OF THE INVENTION

1. Field of the Invention

The present invention relates to a medical apparatus including a first medical device with a bending portion which is provided in an insertion portion and which is bent by a driving force of a driving portion, and a second medical device with an external force applying portion that applies an external force to the insertion portion of the first medical device by means of the driving force of the driving portion so that the insertion portion can operate.

2. Description of the Related Art

In recent years, what is called endoscopic retrograde cholangio pancreatography (hereinafter referred to as ERCP) has been performed in which a diseased site of a canalicus, for example, a diseased site in a pancreaticobiliary system, is examined and treated using a sideward viewing endoscope with an image pickup optical system disposed on a side surface of a distal end of an insertion portion. The ERCP using the sideward viewing endoscope includes examinations in which images of a bile duct or a pancreatic duct are picked up using the endoscope, and therapeutic treatments in which gallstone present in a common bile duct or the like is recovered using a balloon or a treatment instrument.

Since the pancreatic duct and the bile duct are very thin, it is difficult to insert, for the ERCP, the distal end portion of the insertion portion of the endoscope directly into the bile duct or the pancreatic duct. Normally, an operator first inserts the distal end portion of the insertion portion of the sideward viewing endoscope until the distal end portion reaches the vicinity of a duodenal papilla. Thereafter, while observing appropriate sites through the endoscope, the operator draws out any of various endoscopic treatment instruments (hereinafter simply referred to as "treatment instruments") such as a cannulation tube through a treatment instrument insertion tube cavity formed in the side surface of the distal end portion of the insertion portion. The operator then inserts the treatment instrument into the bile duct or the pancreatic duct.

At this time, the operator uses what is called a treatment instrument raising table provided in the vicinity of the opening at the distal end of the treatment instrument insertion tube cavity. A raising angle of the treatment instrument raising table can be varied by a manual operation. Thus, varying the raising angle of the treatment instrument raising table allows a direction in which the treatment instrument is drawn out through the opening to be varied to easily guide the treatment instrument to the bile duct or the pancreatic duct.

For example, an endoscopic device 150 shown in FIG. 1 includes a sideward viewing endoscope 100 and an endoscopic treatment instrument 110. An opening 102a is formed at a distal end portion 102 of an insertion portion 101 of the sideward viewing endoscope 100. An insertion portion 111 of the endoscopic treatment instrument 110, for example, an imaging tube, a high-frequency treatment instrument, or a balloon catheter (hereinafter referred to as the treatment instrument insertion portion in order to distinguish this insertion portion from the insertion portion 101 of the sideward viewing endoscope 100) is drawn out through the opening 102a.

To draw out the treatment instrument insertion portion 111 through the opening 102a and then insert the treatment instrument insertion portion 111 through the bile duct, the operator performs a procedure described below.

First, the operator performs a manual operation of operating a bending knob 104 provided on an operation portion 103 to bend a bending portion (not shown in the drawings), a manual operation of twisting the insertion portion 101, and the like. Thus, the distal end portion 102 is placed opposite a target site, for example, a duodenal papilla 120 in a desired condition.

Then, the operator draws out the treatment instrument insertion portion 111 into a body via a treatment instrument insertion channel (not shown in the drawings) formed in the insertion portion 101 of the sideward viewing endoscope 100 and via a treatment instrument raising table (hereinafter simply referred to as a raising table) 105 located in the vicinity of the opening 102a. Since the raising table 105 has not been raised yet, the treatment instrument insertion portion 111 is thus drawn out as shown by a dashed line or an alternate long and short dash line.

The amount by which the treatment instrument insertion portion 111 is drawn out varies, for example, as shown by the dashed line and the alternate long and short dash line depending on the amount by which the treatment instrument insertion portion 111, positioned close to the operator's hands, is pushed in.

After drawing the treatment instrument insertion portion 111 into the body, the operator operates a raising table operation lever 106. Then, a raising wire (not shown in the drawings) inserted through the insertion portion 101 is pulled. An angle of the treatment instrument raising table 105 is varied in conjunction with this traction. That is, a direction in which the treatment instrument insertion portion 111 is drawn out is changed, for example, from one shown by the alternate long and short dash line to one shown by a solid line. Thus, a distal end 112 of the treatment instrument insertion portion 111 is placed opposite the duodenal papilla 120.

However, in this state, the direction in which the treatment instrument insertion portion 111 is drawn out is toward a pancreatic duct 121. Introducing the treatment instrument insertion portion 111 into a bile duct 122 is thus difficult. Consequently, the operator makes adjustment such as an operation of the bending knob 104, provided on the operation portion 103, to introduce the treatment instrument insertion portion 111 into the bile duct 122.

Thus, the operator needs to be skilled in order to perform the manual operation of placing the distal end portion 102 of the insertion portion 101 of the endoscope 100 opposite the duodenal papilla 120 and smoothly introducing the treatment instrument insertion portion 111 into the pancreatic duct 121 or the bile duct 122.

In recent years, a sideward viewing endoscope with an electric raising table has been proposed in order to improve the operator's workability. This sideward viewing endoscope is configured such that the raising wire is pulled by, for example, a driving motor provided in the operation portion. Furthermore, Japanese Patent Application Laid-Open Publication No. 7-000350 proposes a driving mechanism for a treatment instrument which rotationally drives the raising table into a raising table housing portion in the endoscope distal end portion, the driving mechanism replacing the driving motor provided in the operation portion. According to such a sideward viewing endoscope, the operator operates an inputting portion of the operation portion including switches or buttons to vary the angle of the raising table. Thus, a burden on the operator is reduced.

Also for the treatment instrument, a treatment instrument manipulator has recently been proposed in which the treatment instrument insertion portion includes a bending portion having a plurality of active joints in order to improve the operator's operability. For example, Japanese Patent Application Laid-Open Publication No. 8-224241 discloses a medical manipulator that allows a driving actuator to drive a driving wire. According to the medical manipulator, when the operator operationally tilts a joy stick, a position indicated by the joy stick is inputted to the controller. The controller converts the position into a bending angle and rotation angle of a treatment portion to drive a bending driving actuator and a rotational driving actuator. Then, the bending portion of the medical manipulator is bent to operate the treatment portion in the operator's desired direction. Thus, the operator can easily place the distal end of the treatment instrument opposite the treatment site by operating the joy stick.

As shown in FIG. 2, a sideward viewing endoscope 130 with an electric treatment instrument raising table and a medical manipulator 140 form an endoscopic device 150A. The operator's workability can be drastically improved.

In FIG. 2, reference numeral 131 denotes a raising table angle instruction inputting portion. The operator tilts the raising table angle instruction inputting portion 131, for example, in the direction of arrow a. A driving motor 107 in the operation portion 103 is then driven to pull the raising wire (not shown in the drawings) inserted through the insertion portion 101. Then, the raising table 132 is raised. On the other hand, reference numeral 141 denotes a joy stick for a bending operation provided in a treatment instrument operation portion 142. The joy stick 141 can be operationally tilted, for example, in the direction of arrow c, d, e, or f. In response to the tilting operation of the joy stick 141, driving actuators 143 and 144 in the treatment instrument operation portion 142 are driven. Then, the bending potion 113 is bent, for example, as shown by an alternate one and two short dash line to enable a position of the distal end 112 to be changed.

SUMMARY OF THE INVENTION

A medical apparatus comprises a first medical device, a second medical device, an integrated inputting device, and an integrated control device. The medical device comprises an insertion portion comprising a bending portion that is bent by a driving force of a first driving portion and a first control device drivingly controlling the first driving portion. The second medical device comprises an external force applying portion applying an external force to the insertion portion of the first medical device to move the insertion portion, a second driving portion generating a driving force allowing the external force applying portion to be operated, and a second control device drivingly controlling the second driving portion. The integrated inputting portion instructs a distal end of the insertion portion to be moved to a target position or a target posture or in a target direction, in a configuration in which the external force of the external force applying portion provided in the second medical device can be applied to the insertion portion of the first medical device. The integrated control device drivingly controls at least one of the first driving portion provided in the first medical device and the second driving portion provided in the second medical device on the basis of an instruction from the integrated inputting device.

The above and other objects, features and advantages of the invention will become more clearly understood from the following description referring to the accompanying drawings.

BRIEF DESCRIPTION OF THE DRAWINGS

FIG. 3 is a diagram illustrating the configuration of the medical apparatus;

FIG. 4 is a diagram illustrating the configuration of the treatment instrument insertion portion of the medical manipulator;

FIG. 5 is a diagram illustrating the configuration of the treatment instrument insertion portion of the medical manipulator;

FIG. 6 is a diagram illustrating a distal end portion of the sideward viewing endoscope;

FIG. 7 is a diagram illustrating a treatment instrument channel with a tend-to-curve portion provided in the insertion portion of the sideward viewing endoscope, and the treatment instrument raising table;

FIG. 8 is a diagram illustrating a relationship among joints observed when the treatment instrument insertion portion of the medical manipulator is placed in the treatment instrument channel in a preset posture;

FIG. 9 is a diagram illustrating a state the medical manipulator is inserted through the treatment instrument channel, wherein the tend-to-curve portion of the medical manipulator substantially fits a curving portion of the treatment instrument channel;

FIG. 10 is a diagram illustrating a state where the medical manipulator is inserted through the treatment instrument channel, wherein the tend-to-curve portion of the medical manipulator is displaced from the curving portion of the treatment instrument channel in a major axis direction;

FIG. 11 is a diagram illustrating a state where the treatment instrument insertion portion of the medical manipulator is placed in a preset posture;

FIGS. 12 and 13 are diagrams illustrating a first example of control performed by a control portion;

FIG. 12 is a diagram showing a tilting operation state of an operation lever;

FIG. 13 is a diagram illustrating a tilting operation of the operation lever and an operating state of the joints;

FIGS. 14 and 15 are diagrams illustrating a second example of control performed by the control portion;

FIG. 14 is a diagram showing a tilting operation state of the operation lever;

FIG. 15 is a diagram illustrating a tilting operation of the operation lever and an operating state of the joints;

FIGS. 16 to 19 are diagrams illustrating a third example of control performed by the control portion;

FIG. 16 is a diagram illustrating a state where the operation lever is operationally tilted by an angle $\gamma 1$;

FIG. 17 is a diagram illustrating an operating state of the joints when the operation lever is operationally tilted by the angle $\gamma 1$;

FIG. 18 is a diagram illustrating a state where the operation lever is operationally tilted by an angle $\gamma 2$ exceeding a rotation angle $\theta 1 max$;

FIG. 19 is a diagram illustrating an operational state of respective joints in a state where the operation lever is operationally tilted by the angle $\gamma 2$ exceeding the rotation angle $\theta 1 max$;

FIG. 20 is a diagram illustrating a relationship between a forward viewing endoscope with a raising table and a treatment instrument with a distal bending portion;

FIGS. 21 and 22 are diagrams illustrating another example of the configuration of presetting means;

FIG. 21 is a diagram illustrating a presetting portion and a presetting member which preset a rotation amount around a major axis and a projection amount;

FIG. 22 is a diagram illustrating a state preset by the presetting portion and the presetting member;

FIGS. 23 and 24 are diagrams illustrating another example of the configuration of the presetting means;

FIG. 23 is a diagram illustrating the presetting portion presetting the rotation amount around the major axis and projection amount;

FIG. 24 is a diagram illustrating the presetting member and a preset state in which the presetting member is located in the presetting portion;

FIGS. 25 and 26 are diagrams illustrating yet another example of the configuration of the presetting means;

FIG. 25 is a diagram illustrating an endoscopic image displayed on a screen and a preset state determination frame;

FIG. 26 is a diagram illustrating a relationship between the determination frame and a marking image observed when the treatment instrument insertion portion drawn out of the endoscope is in a preset posture;

FIG. 27 is a diagram illustrating a method of determining whether or not a joint in the distal bending portion projects from a raising joint, on the basis of the endoscopic image displayed on the screen of a display device;

FIG. 28 is a diagram illustrating an example of the configuration of a medical apparatus including a sensor detecting whether or not the joint in the distal bending portion projects from the raising joint;

FIG. 30 is a diagram illustrating another configuration of the medical apparatus;

FIG. 31 is a diagram illustrating a projection amount acquisition mark and a rotation amount acquisition mark provided on a central bending piece;

FIG. 32 is a diagram illustrating the projection amount acquisition mark and rotation amount acquisition mark on the treatment instrument insertion portion as well as a projection amount reference line and a major-axis-direction rotation amount reference line, the marks and reference lines being displayed on the screen; and FIG. 33 is a flowchart illustrating an example of control performed by the control portion.

DETAILED DESCRIPTION OF THE PREFERRED EMBODIMENTS

Embodiments of the present invention will be described with reference to the drawings.

A first embodiment of a medical apparatus will be described with reference to FIGS. 3 to 28.

The medical apparatus will be described with reference to FIGS. 3 to 11.

Figure 3:
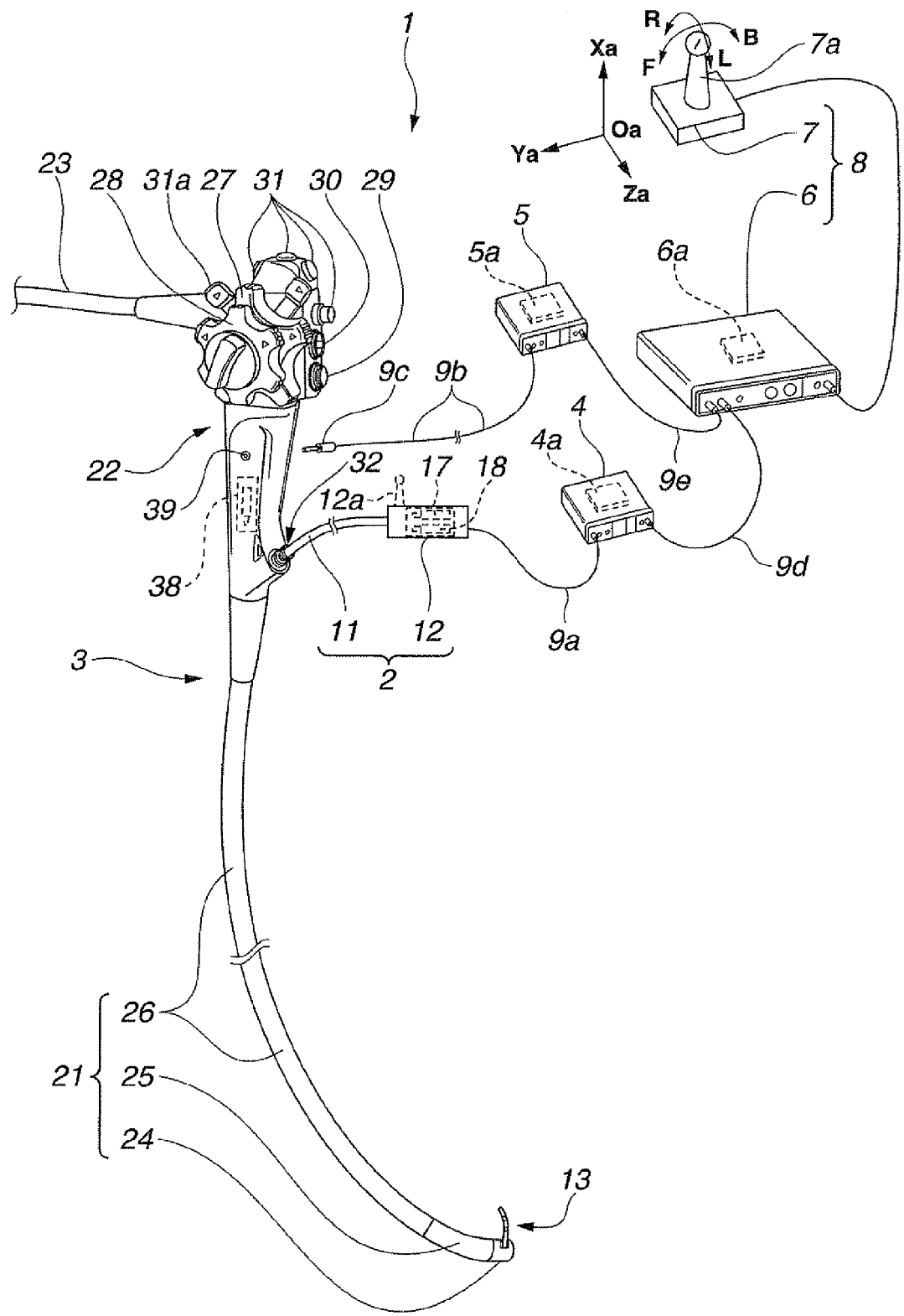
FIGS. 3 to 28 are diagrams illustrating a first embodiment of a medical apparatus.

As shown in FIG. 3, a medical apparatus 1 according to the present embodiment is composed of a medical manipulator (hereinafter simply referred to as a treatment instrument) 2 that is an active treatment instrument, a sideward viewing endoscope (hereinafter simply referred to as an endoscope) 3 with an active raising table (see reference numeral 35 in FIGS. 6 and 7; hereinafter simply referred to as a raising table), and a treatment instrument controller 4, a raising table controller 5 and an integrated controller 6, and an integrated inputting device (hereinafter simply referred to as an inputting device) 7; the controllers and the inputting device are peripheral devices. The inputting device 7 includes, for example, an operationally tiltable operation lever 7a.

The inputting device 7 is, for example, a joy stick and is operationally tiltable in any direction using a base portion of an operation lever 7a as a support point. Specifically, the operation lever 7a is operationally tiltable in the direction of arrow F that is a Ya axis direction in an Oa coordinate system shown in the figures, the direction of arrow B that is a −Ya axis direction, the direction of arrow L that is a Za axis direction, and the direction of arrow R that is a −Za axis direction.

The treatment instrument 2 is a first medical device and includes a treatment instrument insertion portion 11 and a bending driving portion 12. The bending driving portion 12 contains driving actuators 17 and 18 described below and which are first driving portions. The treatment instrument 2 is an imaging tube, a high-frequency treatment instrument, a balloon catheter, and the like.

Figure 4:
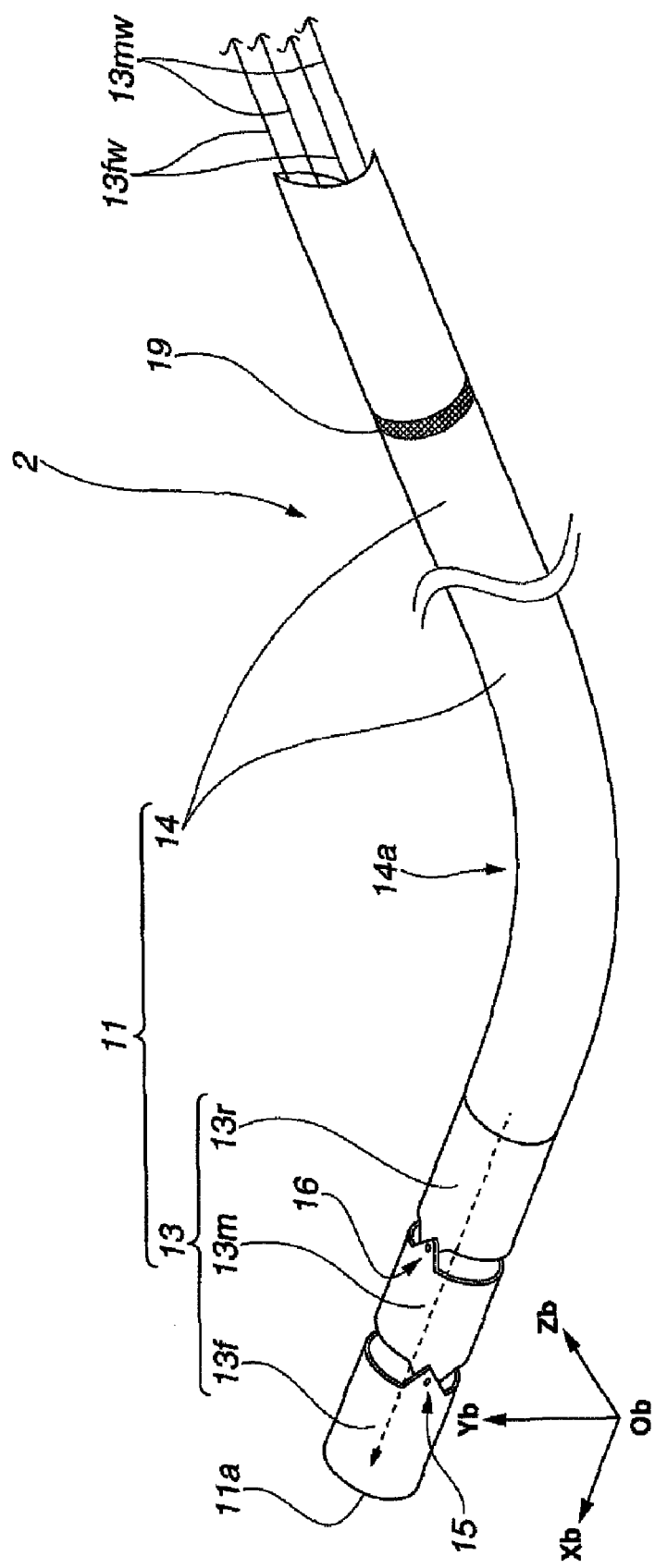

As shown in FIG. 4, the treatment instrument insertion portion 11 includes a distal bending portion 13 and a flexible tube portion 14. The flexible tube portion 14 has a tend-to-curve portion 14a that is presetting means. The tend-to-curve portion 14a is configured to bend at a predetermined radius in a predetermined direction. The tend-to-curve portion 14a of the flexible tube portion 14 is positioned on a proximal end side of the distal bending portion 13. In the present embodiment, the bending shape of the tend-to-curve portion 14a substantially matches a direction in which a first joint 15 described below rotates.

The distal bending portion 13 forms a distal end side of the treatment instrument insertion portion 11. The distal bending portion 13 includes, for example, a distal bending piece 13f, a central bending piece 13m, a proximal bending piece 13r. The distal bending piece 13f and the central bending piece 13m are coupled together by the first joint 15 so as to be pivotally movable. The central bending piece 13m and the proximal bending piece 13r are coupled together by a second joint 16 so as to be pivotally movable.

The first joint 15 is pivotally movable with respect to a Zb axis orthogonal to an Xb axis in an Ob coordinate system in the figures. The second joint 16 is pivotally movable with respect to a Yb axis in the Ob coordinate system. The Xb axis in the Ob coordinate system is parallel to a major axis shown by a dashed line.

Figure 5:
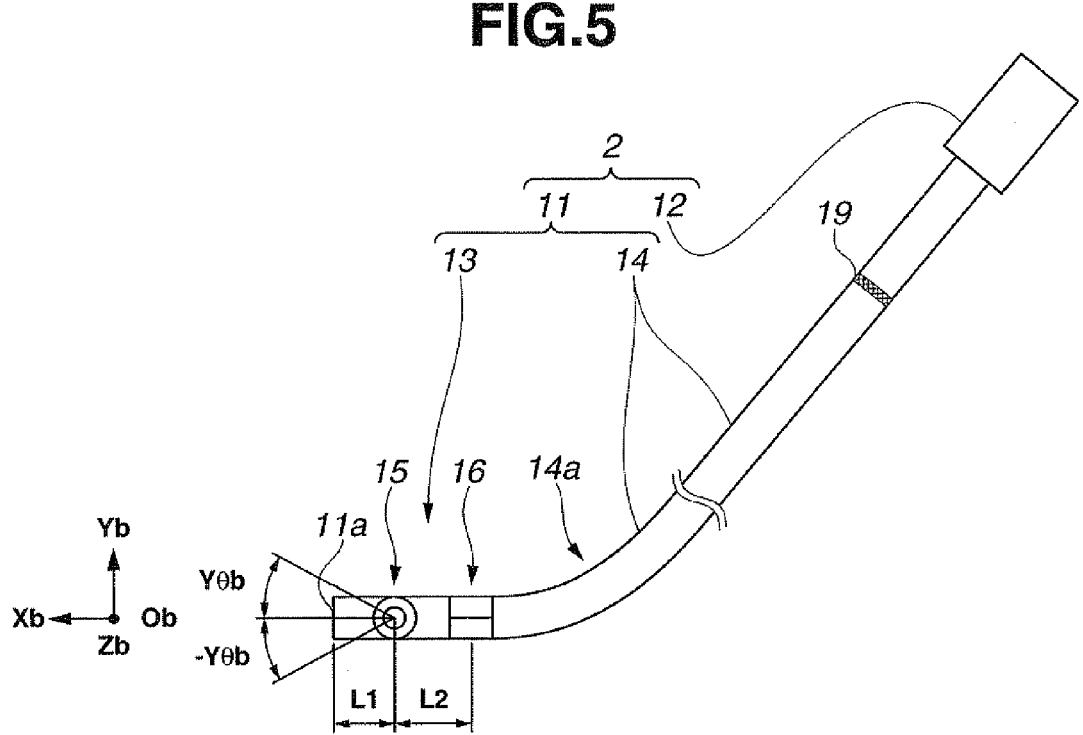

That is, the distal bending piece 13f, coupled to the central bending piece 13m by the first joint 15, is configured to rotate through an angle Yθb in the Yb axis direction and through an angle −Yθb in the −Yb axis direction, with respect to the Xb axis as shown in FIG. 5. A first end and a second end of a distal bending piece wire 13fw are fixed to predetermined positions of the distal bending piece 13f.

A central portion of the distal bending piece wire 13fw is fixedly disposed on a pulley (not shown in the drawings) provided in a bending driving portion 12. The pulley is pivotally moved by a first driving actuator 17, provided in the bending driving portion 12. When the first driving actuator 17 is driven to rotate the pulley, for example, clockwise, a first end of the distal bending piece wire 13fw is pulled, a second end is loosened. Thus, the distal bending piece 13f rotates through, for example, the angle Yθb. In contrast, when the first driving actuator 17 is driven to rotate the pulley counterclockwise, the second end of the distal bending piece wire 13fw is pulled, while the first end is loosened. Thus, the distal bending piece 13f rotates through an angle −Yθb.

On the other hand, the central bending piece 13m, coupled to the proximal bending piece 13r by the second joint 16, is configured to rotate through an angle Zθb in the Zb axis direction and through an angle −Zθb in the −Zb axis direction, with respect to the Xb axis direction. A first end and a second end of a central bending piece wire 13mw are fixed to predetermined positions of the central bending piece 13m.

In FIG. 5, the Zb axis direction is a direction away from the reader, and the −Zb axis direction is a direction toward the reader.

Reference numeral 19 shown in FIGS. 4 and 5 denotes a projection amount detection mark (hereinafter simply referred to as a mark). The mark 19 is presetting means and is composed of, for example, a band-like peripheral line. Alignment of the mark 19 with an opening end in a treatment instrument insertion port 32 described below indicates that the distal end 11a of the treatment instrument insertion portion 11 is drawn out, by a predetermined amount, from an opening 34a in a raising table arrangement space (reference numeral 34 in FIG. 6; hereinafter simply referred to as a table space) provided in a distal end portion 24, described below, of the endoscope 3.

A central portion of the central bending piece wire 13mw is fixedly disposed on the pulley (not shown in the drawings) provided in the bending driving portion 12. The pulley is pivotally moved by a second driving actuator 18, provided in the bending driving portion 12. When the second driving actuator 18 is driven to rotate the pulley, for example, clockwise, a first end of the central bending piece wire 13mw is pulled, a second end is loosened. Thus, the central bending piece 13m rotates through, for example, the angle Zθb. In contrast, when the second driving actuator 18 is driven to rotate the pulley counterclockwise, the second end of the central bending piece wire 13mw is pulled, while the first end is loosened. Thus, the central bending piece 13m rotates through an angle −Zθb.

A distance from a distal end surface of the treatment instrument insertion portion 11 to the first joint 15 is preset to L1. A distance from the first joint 15 to the second joint 16 is preset to L2. In the actual treatment instrument 2, the bending pieces 13f, 13m, and 13r are covered with, for example, an outer tube without being exposed.

The endoscope 3 shown in FIG. 3 includes an insertion portion 21, an operation portion 22, and a universal cord 23. The insertion portion 21 is inserted into a body. The operation portion 22 is provided at a proximal end side of the insertion portion 21. The universal cord 23 extends from the operation portion 22. The universal cord 23 includes an endoscope connector (not shown in the drawings) at a proximal end portion thereof.

The endoscope connector is connected to a light source device that supplies illumination light, for example, via an illumination window described below. An image cable extending from the endoscope connector is connected to a camera control unit (not shown in the drawings). The camera control unit includes an image processing circuit that generates a video signal from an image signal resulting from photoelectric conversion by an image pickup device (not shown in the drawings) provided in the distal end portion of the endoscope 3. The video signal generated by the camera control unit is outputted to the display device. When the video signal is outputted to the display device, an endoscopic image is displayed on the screen of the display device.

The insertion portion 21 is composed of a rigid distal end portion 24, a bending portion 25 that is, for example, bendable upward, downward, rightward, and leftward, and an elongate flexible tube portion 26; the distal end portion 24, the bending portion 25, and the flexible tube portion 26 are connected together in this order from the distal end side.

The operation portion 22 also serves as a gripping portion. The operation portion 22 has a vertical bending knob 27 that bends the bending portion 25 in a vertical direction, a lateral bending knob 28 that bends the bending portion in a lateral direction, an air or water supply button 29, a suction button 30, a plurality of remote buttons 31, and the like. The remote buttons 31 give instructions on, for example, driving control of an image pickup unit or the like (not shown in the drawings) provided in the distal end portion 24. Reference numeral 31a denotes a raising table angle instruction inputting portion that is a second inputting portion.

The operation portion 22 has a treatment instrument insertion port 32 forming a proximal end portion of the treatment instrument channel described below (see reference numeral 33 in FIG. 7). The treatment instrument 2 is adapted to be drawn out through the opening 34a in the distal end portion 24 via the treatment instrument insertion port 32, the treatment instrument channel 33, and the raising table 35.

Reference numeral 38 denotes a driving motor. The driving motor 38 is a second driving portion and moves the raising wire (not shown in the drawings) forward and backward, which operationally raises the raising table 35. Reference numeral 39 denotes an electric connection port. A connector 9c provided on a second connection cord 9b is removably connected to the connection port 39. Connecting the connector 9c to the connection port 39 allows the endoscope 3 to be electrically connected to the raising table controller 5. In the present embodiment, the endoscope 3 is a second medical device.

Figure 6:
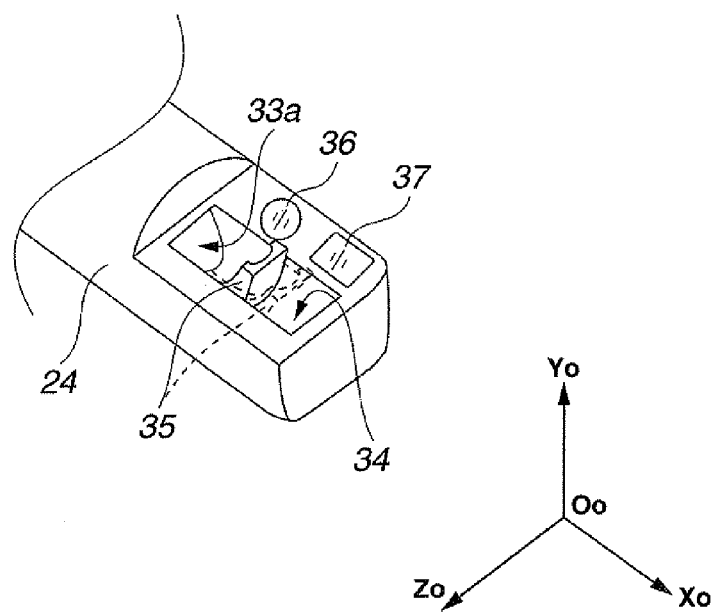
Figure 7:
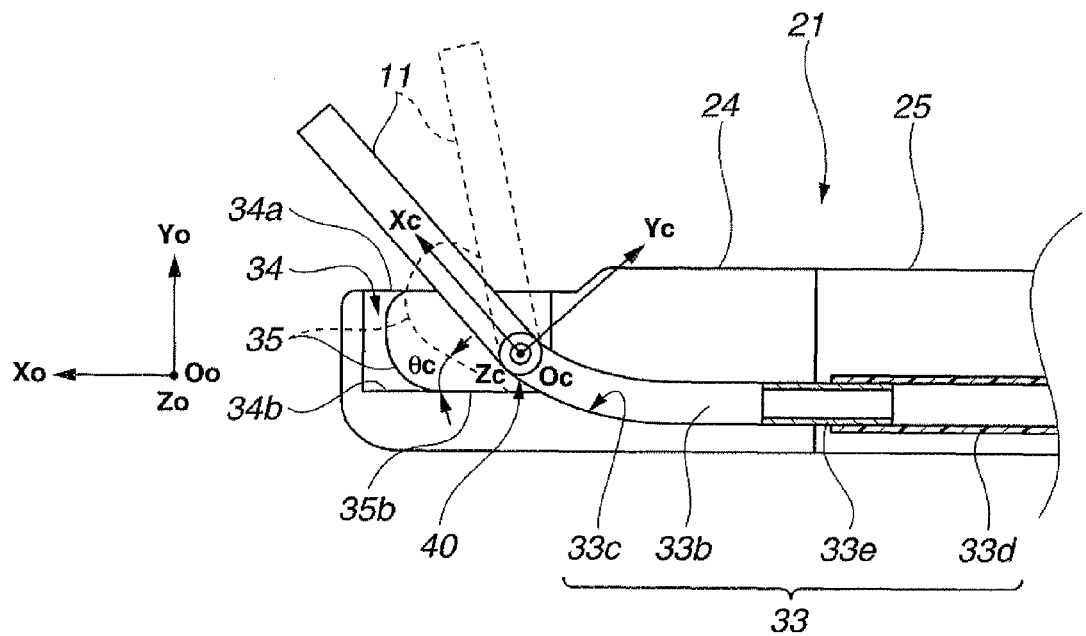

As shown in FIGS. 6 and 7, the distal end portion 24 includes the raising table 35, an observation window 36 forming an observing optical system, and an illumination window 37 forming an illuminating optical system. The raising table 35 is an external force applying portion and is pivotally movably located in the table space 34, formed in the distal end portion 24. The distal opening 33a in the treatment instrument channel 33 communicates with the table space 34.

The raising table 35 has an initial position in which a bottom side surface 35b of the raising table 35 abuts against a bottom surface 34b of the table space 34. The raising table 35 is configured to be pivotally movable with respect to the distal end portion 24 by a raising joint 40. An end portion of the raising wire (not shown in the drawings) is fixed to a predetermined position of the raising table 35.

The raising table 35 is pivotally movable with respect to a Zc axis that is orthogonal to an Xc axis of the Oc coordinate system. The raising table 35 is configured to rotate through an angle Yθc in a Yc axis direction with respect to the Xc axis. The Xc axis in the Oc coordinate system is parallel to a treatment instrument guiding direction in which the treatment instrument 2 is drawn out when the raising table 35 is located in the initial position.

When the raising wire inserted through the insertion portion 21 is pulled in the major axis direction by the driving motor 38, the raising angle of the raising table 35 is varied in increments of the angle Yθc, for example, as shown by a dashed line. In this state, when the raising wire that has been being pulled by the driving motor 38 is loosened, the raising table 35 moves gradually toward the initial position as the raising wire loosens.

As shown in FIG. 7, a channel hole 33b forming the treatment instrument channel 33 is formed in the distal end portion 24. A cap 33e is fixedly disposed on a proximal end side of the channel hole 33b. A distal end portion of a channel tube 33d is fixedly disposed on the cap 33e.

A curving portion 33c shaped to be bent at a predetermined radius is formed on the distal opening 33a side of the channel hole 33b. The curving portion 33c is presetting means. A direction in which the curving portion 33c is bent substantially matches a direction in which the raising joint 40 rotates. A bending shape of the curving portion 33c substantially matches a bending shape of the tend-to-curve portion 14a of the flexible tube portion 14, forming the treatment instrument insertion portion 11.

Thus, when the treatment instrument insertion portion 11 is inserted through the treatment instrument channel 33 as shown in FIG. 6, the mark 19 aligns with the opening end of the treatment instrument insertion port 32 to place the tend-to-curve portion 14a on the curving portion 33c. Thus, the treatment instrument insertion portion 11 is drawn out of the opening 34a in the endoscope 3 at a preset posture. A distance between the raising joint 40 and the second joint 16 is preset to L3.

In the present embodiment, a rotating direction of the first joint 15 is preset to be the same as that of the raising joint 40. This is because the Ob coordinate system for the first joint 15 substantially matches the Oc coordinate system for the raising joint 40.

In the present embodiment, the configuration in which the curving potion 33c is formed in the channel hole 33b is illustrated. However, in a configuration in which the channel tube 33d extends to the distal opening 33a, a tend-to-curve portion corresponding to the tend-to-curve portion 14a of the flexible tube portion 14 is provided on the distal opening 33a side of the channel tube 33d.

In the above description, the bending portion 25 is bent in the vertical direction and the lateral direction. The upward direction corresponds to a Yo axis direction in an Oo coordinate system shown in FIGS. 6 and 7. The downward direction corresponds to a −Yo axis direction that is opposite to the Yo axis direction. On the other hand, the rightward direction corresponds to a Zo axis direction in the Oo coordinate system. The leftward direction corresponds to a −Zo axis direction that is opposite to the Zo axis direction. In FIG. 7, the Zo axis direction is a direction away from the reader, and the −Zo axis direction is a direction toward the reader.

Figure 1:
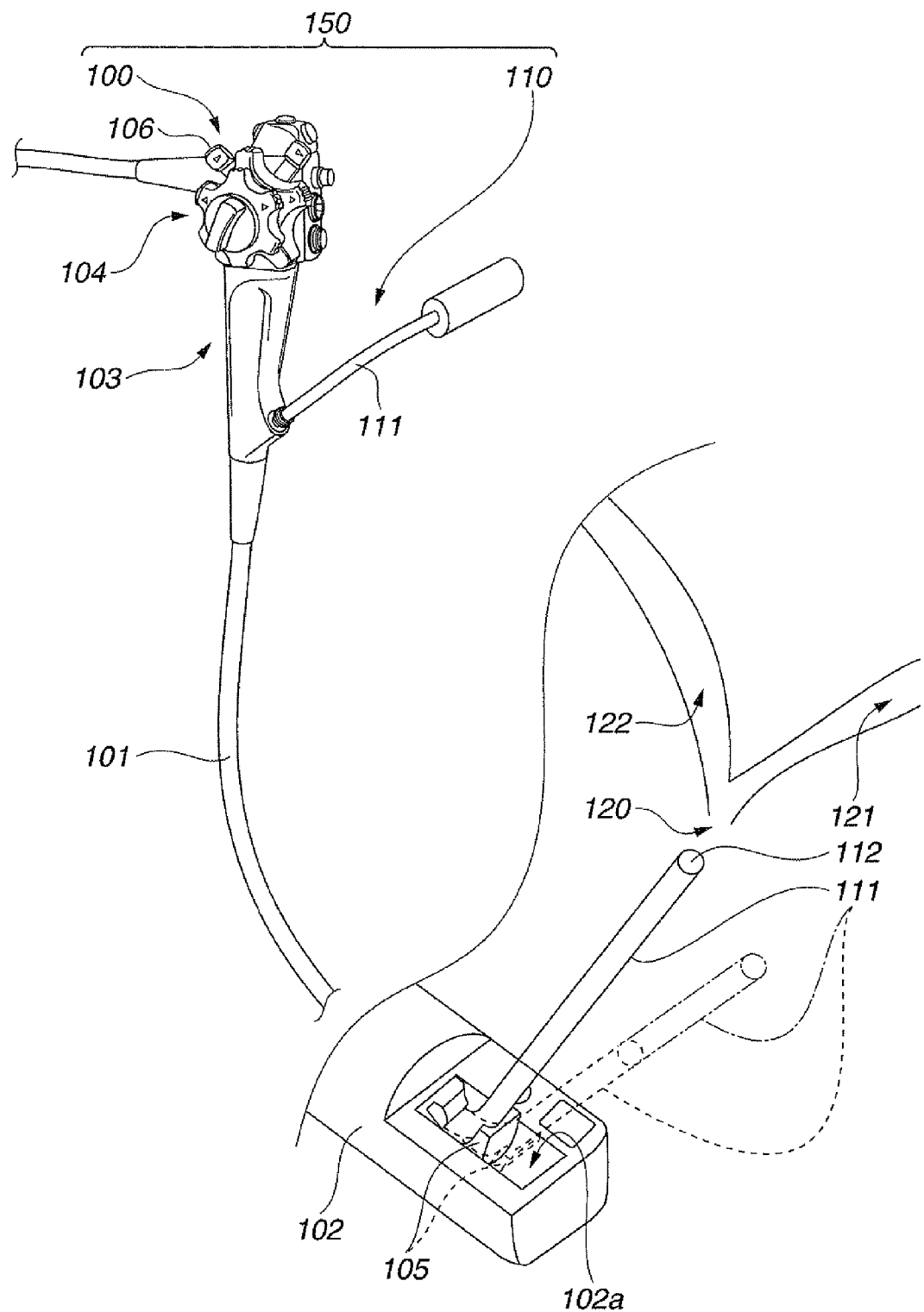
FIG. 1 is a diagram illustrating an endoscopic device including a sideward viewing endoscope and an endoscope treatment instrument.
Figure 2:
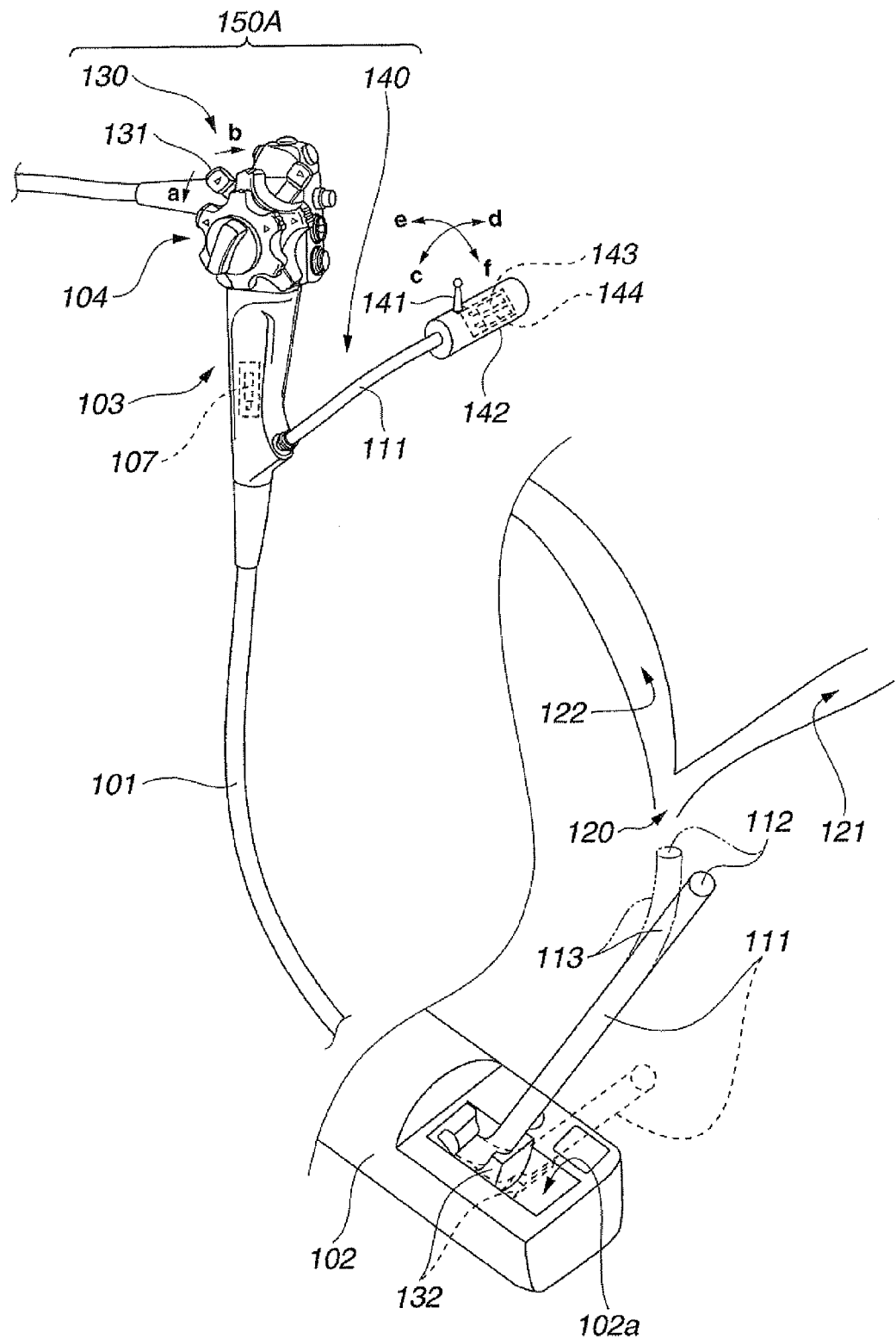
FIG. 2 is a diagram illustrating an endoscopic device including a sideward viewing endoscope with an electric treatment instrument raising tables and a medical manipulator.

The treatment instrument controller 4 shown in FIG. 1 is a first control device. The treatment instrument controller 4 includes a control portion 4a. The control portion 4a controls driving of the actuators 17 and 18 of the treatment instrument 2 to move the distal end 11a in the vertical direction or the lateral direction.

The treatment instrument controller 4 is electrically connected to the bending driving portion 12 via the first connection cord 9a. For example, the inputting device 7 can be connected to the treatment instrument controller 4. By connecting the inputting device 7 to the treatment instrument controller 4, and in this state, operationally tilting the operation lever 7a of the inputting device 7, the distal end 11a can be moved in the vertical direction, the lateral direction, or a synthesis direction of the vertical and lateral directions.

Specifically, for example, when the operator operationally tilts the operation lever 7a of the inputting device 7 in the direction of arrow F, the first driving actuator 17, provided in the treatment instrument 2, is driven. Then, the distal bending piece 13f, located parallel to the Xb axis, rotates in the Yb axis direction in association with an angle through which the operation lever 7a has been tilted. In contrast, when the operator operationally tilts the operation lever 7a in the direction of arrow B, the first driving actuator 17 is driven to rotate the distal bending piece 13f in the −Yb axis direction in association with the angle through which the operation lever 7a has been tilted.

On the other hand, when the operator operationally tilts the operation lever 7a in the direction of arrow R, the second driving actuator 18 is driven to rotate the central bending piece 13m located parallel to the Xb axis, in the Zb axis direction in association with the angle through which the operation lever 7a has been tilted. In contrast, when the operator operationally tilts the operation lever 7a in the direction of arrow L, the second driving actuator 18 is driven to rotate the central bending piece 13m in the −Zb axis direction in association with the angle through which the operation lever 7a has been tilted.

The raising table controller 5 is a second control device. The raising table controller 5 includes a control portion 5a. The control portion 5a controls driving of the driving motor 38, provided in the endoscope 3, to vary the raising angle of the raising table 35.

The raising table controller 5 is electrically connected to the driving motor 38 in the operation portion 22 via the second connection cord 9b. For example, the inputting device 7 can also be connected to the raising table controller 5. The raising table 35 can be operated by connecting the inputting device 7 to the raising table controller 5, and in this state, operationally tilting the operation lever 7a of the inputting device 7 in the direction of arrow F or arrow B.

Specifically, for example, when the operator operationally tilts the operation lever 7a of the inputting device 7 in the direction of arrow F, the driving motor 38, provided in the endoscope 3, is driven to pull the raising wire inserted through the insertion portion 21. Then, the raising table 35 rotates in the Yc axis direction in association with the angle through which the operation lever 7a has been tilted. In contrast, when the operator operationally tilts the operation lever 7a of the inputting device 7 in the direction of arrow B, the driving motor 38 is driven in the opposite direction. At this time, with the bottom side surface 35b of the raising table 35 not abutting against the bottom surface 34b of the table space 34, the raising table 35 rotates in the −Yc axis direction as the raising wire loosens. If the bottom side surface 35b of the raising table 35 abuts against the bottom surface 34b of the table space 34 when the operator operationally tilts the operation lever 7a in the direction of arrow B, the driving motor 38 remains stopped.

The integrated controller 6 is an integrated control device. The integrated controller 6 includes a control portion 6a. The integrated controller 6 is combined with the inputting device 7 to constitute an integrated medical device 8. That is, with the treatment instrument controller 4 and the raising table controller 5 connected to the integrated medical device 8, the control portion 6a drivingly controls the actuators 17 and 18, provided in the treatment instrument 2, and the driving motor 38 provided in the endoscope 3.

Specifically, when the operator operationally tilts the operation lever 7a of the inputting device 7 in the direction of arrow F or arrow B, the control portion 6a drives at least one of the first driving actuator 17 and the driving motor 38. On the other hand, when the operator operationally tilts the operation lever 7a in the direction of arrow R or arrow L, the control portion 6a drives the second driving actuator 18.

In the present embodiment, when the inputting device 7, the treatment instrument controller 4, and the raising table controller 5 are connected to the integrated controller 6, the function of the raising table angle instruction inputting portion 31a and the function of a joy stick 12a are off; the raising table angle instruction inputting portion 31a is provided in the endoscope 3, and the joy stick 12a is shown by a dashed line and is a first inputting portion provided in the bending driving portion 12.

Furthermore, in the present embodiment, the treatment instrument controller 4 and the integrated controller 6 are connected together by a first signal cable 9d. The raising table controller 5 and the integrated controller 6 are connected together by a second signal cable 9e. However, the connection between the treatment instrument controller 4 and the integrated controller 6 and the connection between the raising table controller 5 and the integrated controller 6 may be established by one type of signal cable rather than by the separate signal cables.

The operation of the medical apparatus 1 configured as described above will be described.

First, to construct the medical apparatus 1 shown in FIG. 1, a medical staff member (hereinafter referred to as a staff member) performs an operation of connecting the treatment instrument controller 4 and the bending driving portion 12 of the treatment instrument 2, an operation of connecting the raising table controller 5 and the endoscope 3 together, an operation of connecting the treatment instrument controller 4 to the integrated controller 6, an operation of connecting the raising table controller 5 to the integrated controller 6, and an operation of connecting the inputting device 7 to the integrated controller 6. Thus, the medical apparatus 1 is constructed.

Then, to diagnose or treat the bile duct, the pancreatic duct, or the like, the operator orally inserts the insertion portion 21 of the endoscope 3 until the insertion portion 21 reaches the duodenal bulb. At this time, observing an endoscopic image displayed on the screen of the display device (not shown in the drawings), the operator appropriately performs an operation of bending the bending portion 25 using the bending knobs 27 and 28, an operation of twisting the insertion portion 21, and the like. The operator guides the distal end portion 24 to the vicinity of an opening in the papilla.

Then the operator, for example, instructs the staff member to use the treatment instrument 2. In response to the instruction, the staff member inserts the distal end 11a of the treatment instrument insertion portion 11 of the treatment instrument 2 through the treatment instrument insertion port 32. Thereafter, the staff member pushes in the treatment instrument insertion portion 11. Then, the treatment instrument insertion portion 11 is inserted through the channel tube 33d with a proximal end in communication with the treatment instrument insertion port 32. As the staff member inserts the treatment instrument insertion portion 11 toward the distal end of the channel tube 33d, the tend-to-curve portion 14a of the flexible tube portion 14 abuts against the treatment instrument insertion port 32.

Then, the staff member continues to push in the treatment instrument insertion portion 11 against the elastic force of the tend-to-curve portion 14a. The tend-to-curve portion 14a is then deformed and passes through the treatment instrument insertion port 32. The tend-to-curve portion 14a is then inserted through the channel tube 33d.

Figure 9:
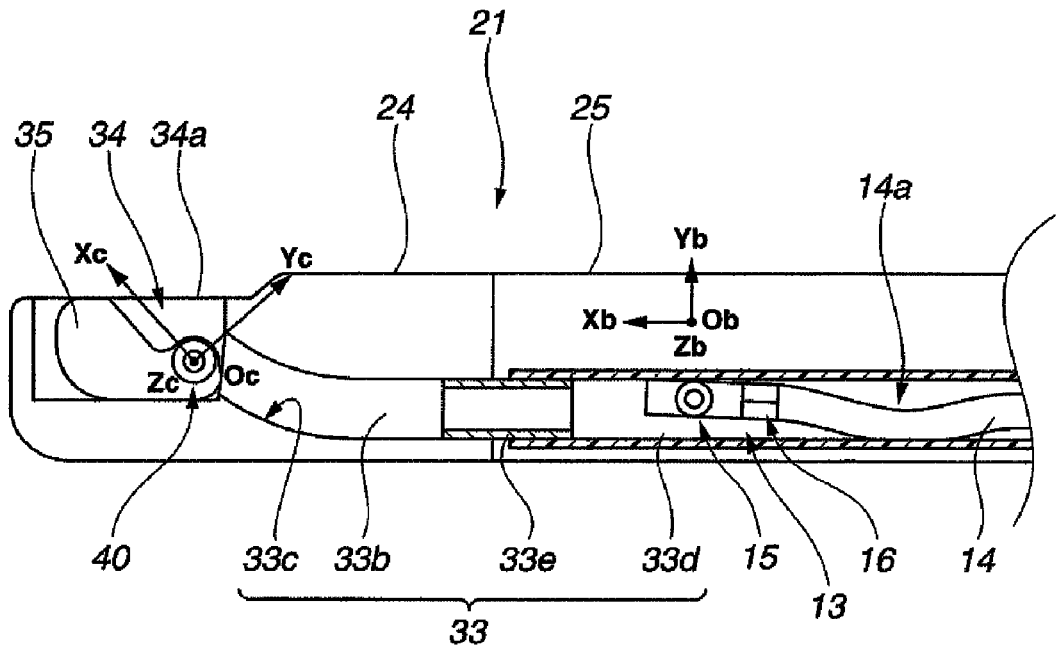

Also in this case, as shown in FIG. 9, one side portion of the tend-to-curve portion 14a contacts an inner surface of the channel tube 33d by the elastic force. With the one side portion of the tend-to-curve portion 14a in contact with the inner surface of the channel tube 33d, the staff member further pushes the distal end 11a of the treatment instrument insertion portion 11 toward the distal opening 33a. During this operation, the staff member checks whether or not the projection amount detection mark 19 has reached the vicinity of the opening end of the treatment instrument insertion port 32.

Figure 8:
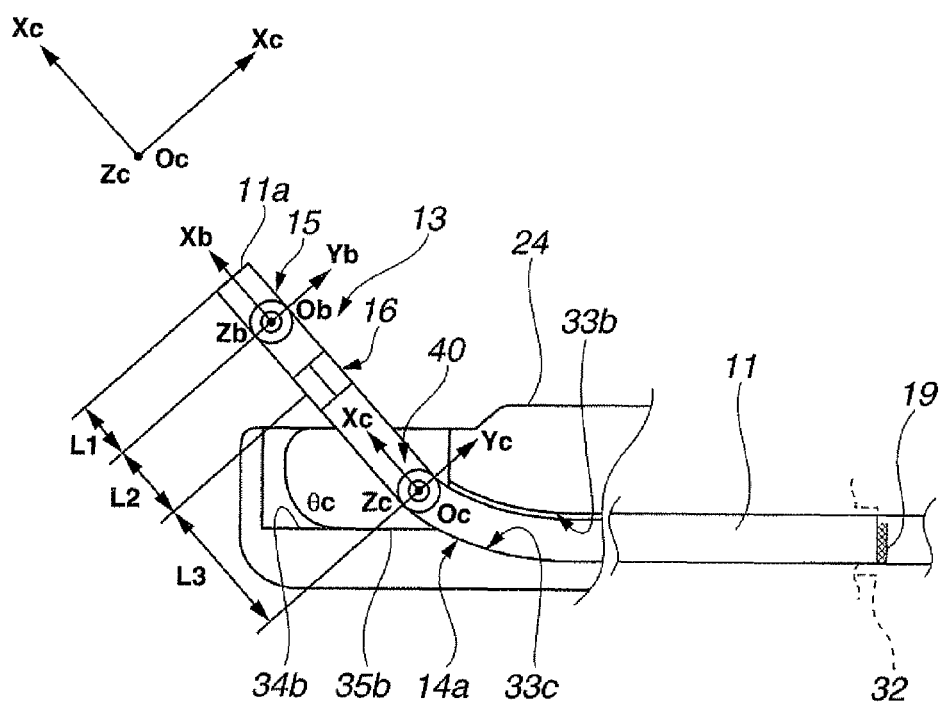

When the projection amount detection mark 19 approaches the opening end of the treatment instrument insertion port 32 and if the bending shape of the tend-to-curve portion 14a of the treatment instrument insertion portion 11 substantially matches the bending shape of the curving portion 33c of the treatment instrument channel 33 as shown in FIG. 9, the staff member's push-in operation fits the tend-to-curve portion 14a into the curving portion 33c. Then, as shown in FIG. 8, the treatment instrument insertion portion 11 is drawn out of the endoscope 3 in a preset posture. At this time, the distal end 11a of the treatment instrument insertion portion 11 and a part of the distal bending portion 13 are displayed on the screen of the display device in a given posture. Thus, the insertion of the treatment instrument insertion portion 11 into the treatment instrument channel 33 is completed.

Figure 10:
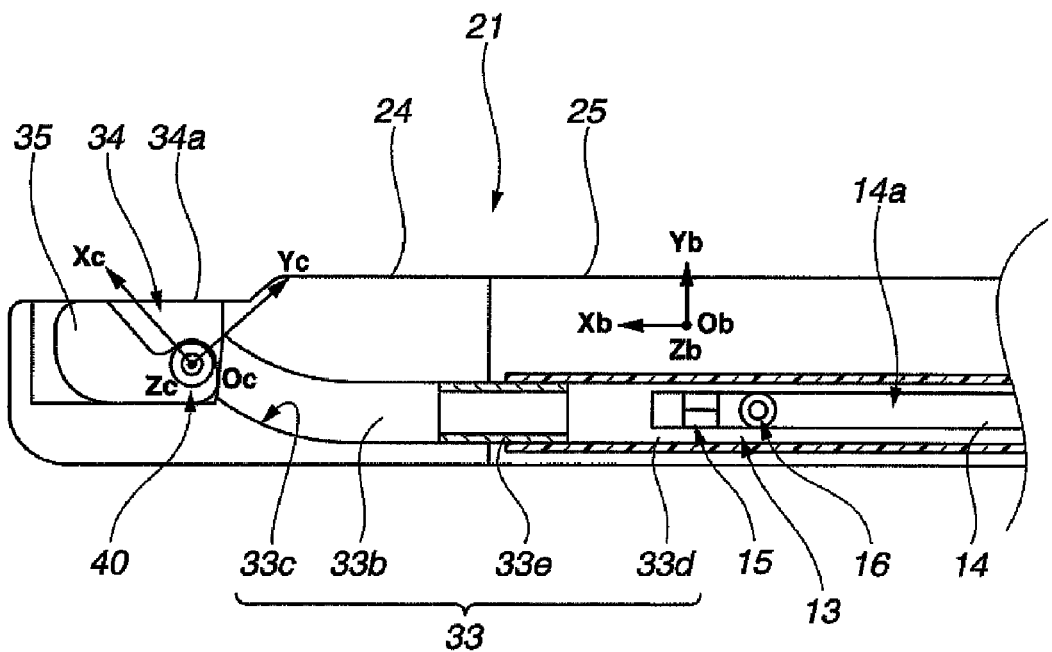

If the position of the tend-to-curve portion 14a of the treatment instrument insertion portion 11 is displaced from the position of the curving portion 33c of the treatment instrument channel 33 as shown in FIG. 10 while the treatment instrument insertion portion 11 is passing through the channel tube 33d, the treatment instrument insertion portion 11 is rotated around the major axis so that the positional energy of the tend-to-curve portion 14a is minimized as the projection amount detection mark 19 approaches the opening end of the treatment instrument insertion port 32. In other words, the treatment instrument insertion portion 11 is rotated around the major axis so that the bending shape of the tend-to-curve portion 14a substantially matches the bending shape of the curving portion 33c as the tend-to-curve portion 14a approaches the curving portion 33c. As a result, when the projection amount detection mark 19 aligns with the opening end of the treatment instrument insertion port 32, the tend-to-curve portion 14a is placed in the curving portion 33c, with the treatment instrument insertion portion 11 drawn out of the endoscope 3 in the preset posture, as described above.

Figure 11:
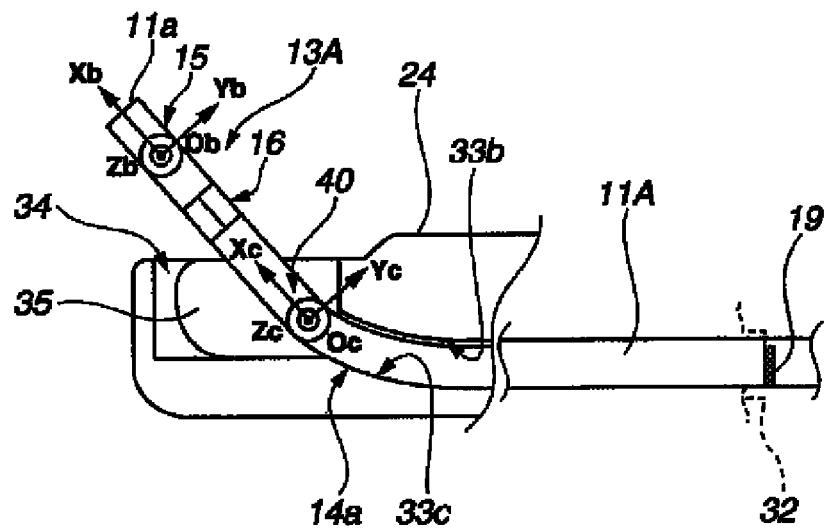

A state in which the treatment instrument insertion portion 11 is drawn out of the endoscope 3 in the preset posture is considered to be a state in which a treatment instrument insertion portion 11A having a distal bending portion 13A including the three joints 15, 16, and 40 is drawn out of the endoscope 3 as shown in FIG. 11. Two of the three joints 15, 16, and 40, that is, the joints 15 and 40, are configured to rotate in the same direction.

Upon determining that the treatment instrument insertion portion 11 has been drawn out of the endoscope 3 in the preset posture, the operator operates the operation lever 7a of the inputting device 7 to guide the distal end 11a of the treatment instrument insertion portion 11 to the opening in the papilla.

When the operator operationally tilts the operation lever 7a, a target bending direction and a target angle are inputted to the control portion 6a of the integrated controller 6. The control portion 6a controls the joints 15, 16, and 40 according to a control method described below, to achieve the target bending direction and the target angle.

Positional information outputted by an encoder, a potentiometer, or the like provided in each of the driving actuators 17 and 18 and the driving motor 38 is inputted to the integrated controller 6. Then, the control portion 6a uses the positional information to control the joints 15, 16, and 40 in association with the operation of the operation lever 7a.

Now, with reference to FIGS. 12 to 19, description will be given of examples of control performed by the control portion 6a of the integrated controller 6, provided in the medical apparatus 1 according to the first embodiment.

A first example of control performed by the control portion 6a will be described with reference to FIGS. 12 and 13.

Figure 12:
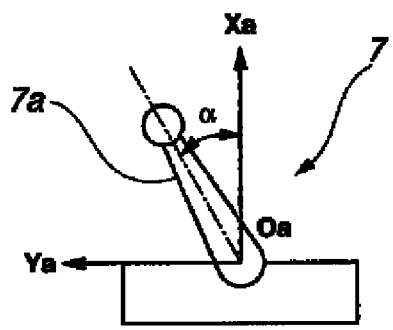
Figure 13:
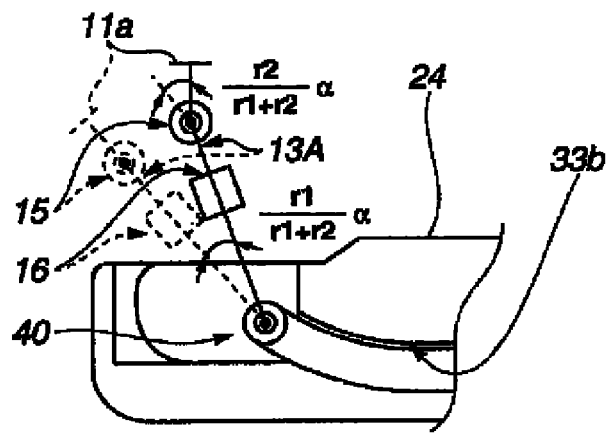

It is assumed that as shown in FIG. 12, the operator operationally tilts the operation lever 7a in the Ya axis direction, that is, the direction F, through an angle α with respect to the Xa axis. Then, in the present embodiment, the control portion 6a operates the joints 15 and 40 on the basis of a preset ratio of, for example, r1:r2.

Specifically, when the operation lever 7*a* is operationally tilted, the control portion 6*a* of the integrated controller 6 outputs control signals to the control portion 4*a* of the treatment instrument controller 4 and the control portion 5*a* of the raising table controller 5. Then, as shown in FIG. 13, the control portion 5*a* rotates the raising joint 40 through a rotation angle $\theta 1$, and the control portion 4*a* rotates the joint 15 through a rotation angle $\theta 3$. Here, the rotation angle $\theta 1 = (r1/(r1+r2))\alpha$, and the rotation angle $\theta 3 = (r2/(r1+r2))\alpha$.

Thus, the distal bending portion 13A in a preset posture shown by a dashed line is bent. The distal end 11*a* of the treatment instrument insertion portion 11 is moved in a target bending direction through a target angle; the target bending direction and the target angle are specified by the tilting operation of the operation lever 7*a*.

In the present embodiment, as described above, when the operation lever 7*a* is operationally tilted in the direction F or B, the joints 15 and 40 are rotated in the direction in which the operation lever 7*a* has been tilted, in association with the tilting angle of the operation lever 7*a*. In contrast, when the operation lever 7*a* is operationally tilted in the direction R or L, the second joint 16 is rotated in the direction in which the operation lever 7*a* has been tilted, in association with the tilting angle of the operation lever 7*a*.

A second example of control performed by the control portion 6*a* will be described with reference to FIGS. 14 and 15.

Figure 14:
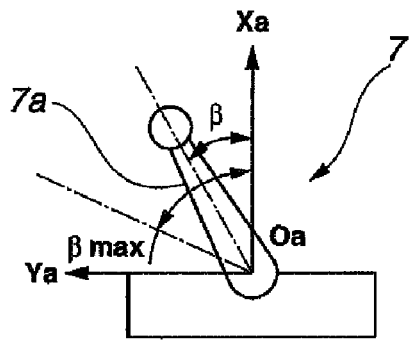
Figure 15:
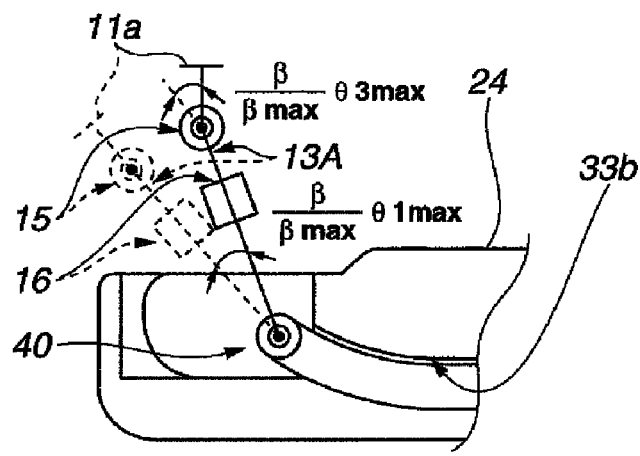

It is assumed that as shown in FIG. 14, the operator operationally tilts the operation lever 7*a* in the Ya axis direction, that is, the direction F, through an angle $\beta$. Then, in the present embodiment, the control portion 6*a* operates the joints 15 and 40 on the basis of a preset ratio, that is, the ratio of the tilting angle $\beta$ of the operation lever 7*a* to a maximum bending angle $\beta$max of the operation lever 7*a*.

Specifically, when the operation lever 7*a* is operationally tilted, the control portion 6*a* of the integrated controller 6 outputs control signals to the control portion 4*a* of the treatment instrument controller 4 and the control portion 5*a* of the raising table controller 5. Then, as shown in FIG. 15, for example, the control portion 5*a* rotates the raising table joint 40 through the rotation angle $\theta 1$. The control portion 4*a* rotates the joint 15 through the rotation angle $\theta 3$. Here, the rotation angle $\theta 1 = (\beta/\beta\text{max})\,\theta 1\text{max}$ and the rotation angle $\theta 3 = (\beta/\beta\text{max})\,\theta 3\text{max}$.

$\theta 1$max denotes the maximum bending angle of the raising joint 40, and $\theta 3$max denotes the maximum bending angle of the joint 15.

Thus, the distal bending portion 13A is bent from a preset posture shown by a dashed line. The distal end 11*a* of the treatment instrument insertion portion 11 is moved in a target bending direction through a target angle; the target bending direction and the target angle are specified by the tilting operation of the operation lever 7*a*.

Also in the present embodiment, when the operation lever 7*a* is operationally tilted in the direction R or L, the second joint 16 is rotated in the direction in which the operation lever 7*a* has been tilted, in association with the tilting angle of the operation lever 7*a*.

A third example of control performed by the control portion 6*a* will be described with reference to FIGS. 16 to 19.

Figure 16:
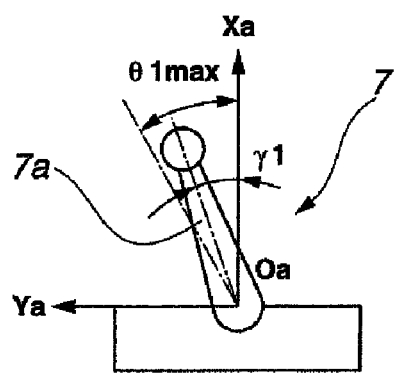

It is assumed that as shown in FIG. 16, the operator operationally tilts the operation lever 7*a* in the Ya axis direction, that is, the direction F, through an angle $\gamma 1$. Then, in the present embodiment, the control portion 6*a* first determines whether or not the angle $\gamma 1$ is greater than $\theta 1$max.

Figure 17:
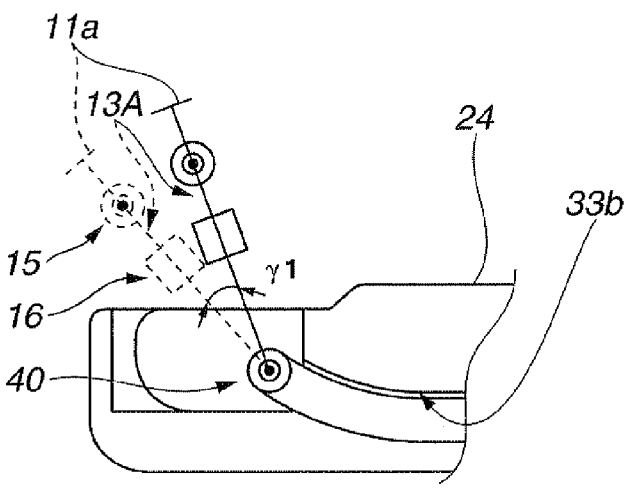

In a tilting state shown in FIG. 16, the control portion 6*a* determines that the angle $\gamma 1$ less or equal to $\theta 1$max. Then, on the basis of the determination, the control portion 6*a* outputs a control signal to the control portion 5*a* of the raising table controller 5. Only the raising joint 40 is thus rotated through the rotation angle $\theta 1$, that is, the rotation angle $\theta 1 =$ the angle $\gamma 1$ as shown in FIG. 17.

Figure 18:
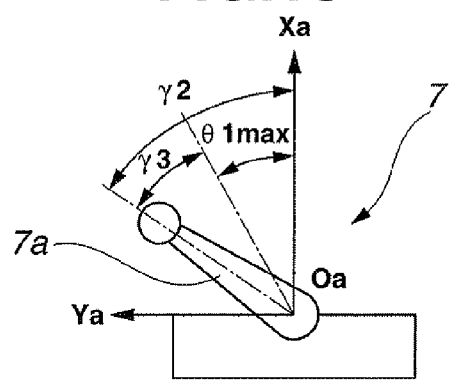
Figure 19:
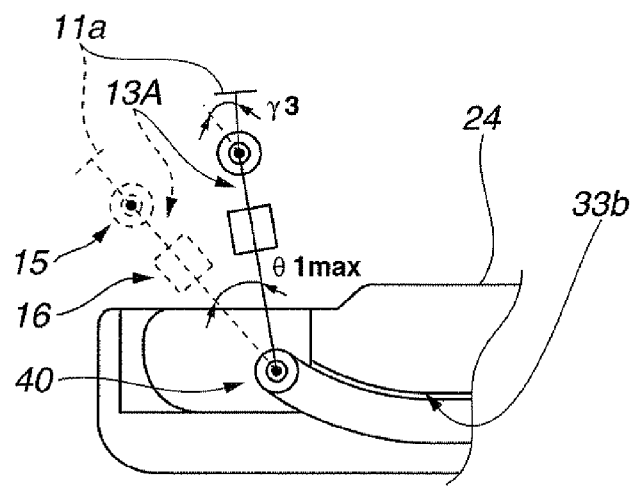

On the other hand, if the control portion 6*a* determines that an angle $\gamma 2$ is greater or equal to $\theta 1$max as shown in FIG. 18, the control portion 6*a* obtains an angle $\gamma 3$ that is a difference between the angle $\gamma 2$ and $\theta 1$max. After calculating the difference, the control portion 6*a* outputs control signals to the control portion 4*a* of the treatment instrument controller 4 and the control portion 5*a* of the raising table controller 5. Then, as shown in FIG. 19, the control portion 5*a* rotates the raising joint 40 through $\theta 1$max. The control portion 4*a* then rotates the joint 15 through the rotation angle $\theta 3 =$ the angle $\gamma 3$.

Thus, the distal bending portion 13A is bent from a preset posture shown by a dashed line. The distal end 11*a* of the treatment instrument insertion portion 11 is moved in a target bending direction through a target angle; the target bending direction and the target angle are specified by the tilting operation of the operation lever 7*a*.

Also in the present embodiment, when the operation lever 7*a* is operationally tilted in the direction R or L, the second joint 16 is rotated in the direction in which the operation lever 7*a* has been tilted, in association with the tilting angle of the operation lever 7*a*.

Thus, by providing the integrated medical device including the integrated controller and the inputting device, control can be performed according to the direction and angle specified by the inputting device such that the raising table of the endoscope and the treatment instrument bending portion are electrically driven in conjunction with each other to achieve wide ranges of target directions and target angles by means of simpler operations. In other words, the electric driving portions provided in the two medical devices can be controlled as an electric driving portion provided in one medical device.

Furthermore, the treatment instrument insertion portion of the treatment instrument has the tend-to-curve portion of the predetermined shape. On the other hand, the treatment instrument channel of the endoscope has the curving portion with the shape matching the shape of the tend-to-curve portion. Thus, matching the tend-to-curve portion with the curving portion allows the projection amount of the treatment instrument insertion portion and the rotating direction of the treatment instrument insertion portion around the major axis to be set to a preset state. Thus, a relationship between the joint in the distal bending portion of the treatment instrument insertion portion and the joint in the raising table can be preset to allow the inputting device to be operated with a relationship maximizing the movable range, a relationship for a direction requiring the maximum bending angle, and the like always maintained in the same state.

The integrated controller 6 may have a switch to allow one of a plurality of operation states to be selected. For example, one of three operation states described below may be selected using the switch. In a first operation state, the medical device including the distal bending portion 13 and the medical device including the raising table 35 can be drivingly controlled by operationally tilting the operation lever 7*a*. In a second operation state, only the medical device including the distal bending portion 13 can be drivingly controlled by operationally tilting the operation lever 7*a*. In a third operation state, the medical device including the raising table 35 can be drivingly controlled by operationally tilting the operation lever 7*a*. According to this configuration, when the operator appropriately operates the switch during operation, the distal end 11a of the treatment instrument insertion portion 11 can be more easily bent into a target site.

In the present embodiment, the inputting device 7, connected to the integrated controller 6 forming the integrated medical device 8, is provided separately from the endoscope 3 and the like as a joy stick. However, the inputting device 7 is not limited to the device separate from the endoscope 3. The inputting device 7 may be provided in the operation portion 22 of the endoscope 3. This configuration allows the operator's hand gripping the operation portion 22 to also operate the joy stick, drastically improving operability.

Furthermore, the inputting device 7 is not limited to the joy stick but may be a track ball or the like.

Moreover, in the present embodiment, the inputting device 7, the treatment instrument controller 4, and the raising table controller 5 are connected to the integrated controller 6, forming the integrated medical device 8. However, the control portion of the integrated controller may have the function of the control portion 4a of the treatment instrument controller 4 and the function of the control portion 5a of the raising table controller 5. According to this configuration, the single integrated controller can be used instead of the controllers for the medical apparatus, thus simplifying the medical apparatus. This also eliminates the need to connect the controllers together and allows the single integrated controller to directly control the rotation of the distal bending portion of the treatment instrument insertion portion and the rotation of the raising table.

Furthermore, the actuator bending the joint may be an ultrasound actuator, a piezoelectric actuator, a magnetostrictive actuator, a polymer actuator, a fluid pressure actuator using air, water, or the like, or a shape memory alloy or an artificial muscle.

The degree of freedom of the raising table, and the degree of freedom of the distal bending portion provided in the treatment instrument insertion portion is not limited to those described above in the embodiment. Different degrees of freedom may be used for the raising table and the distal bending portion.

The bending structure of the distal bending portion may be a structure in which three or more bending pieces are consecutively connected together so as to be pivotally movable.

The ratio of bending driving of the raising table to bending driving of the distal bending portion of the treatment instrument insertion portion is not limited to the preset ratio. Alternatively, a setting portion may be provided in the integrated controller so as to be able to vary the ratio.

The endoscope is not limited to the sideward viewing endoscope but may be a forward viewing endoscope in which an observing optical system is located forward in the major axis direction, a rigid endoscope, or the like.

Figure 20:
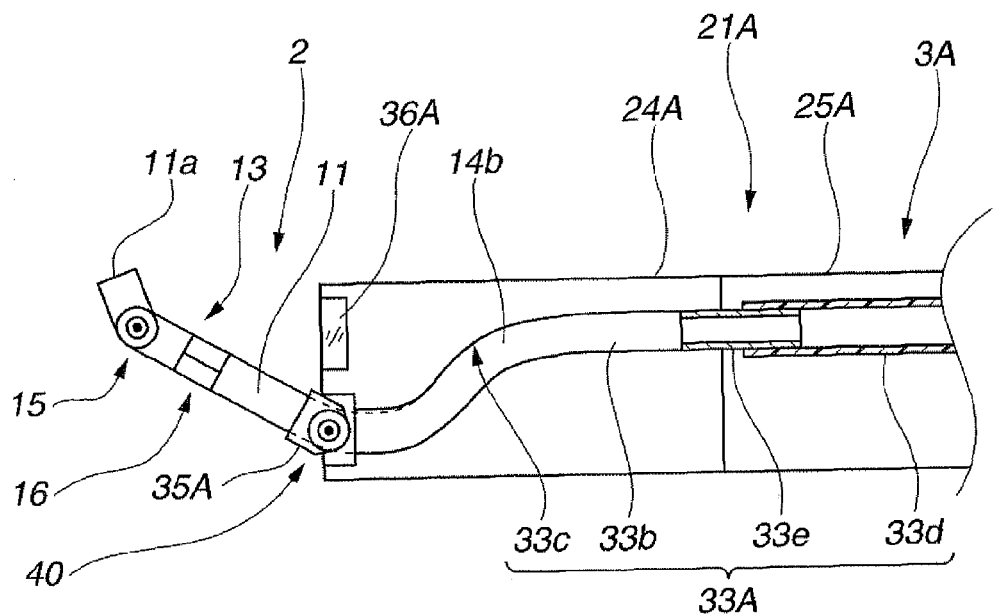

As shown in FIG. 20, a raising table 35A including the joint 40 may be provided in a forward viewing endoscope 3A including a forward viewing window 36A. The forward viewing endoscope 3A has a distal end portion 24A, a bending portion 25A, and an insertion portion 21A including a flexible tube portion (not shown in the drawings). A channel hole 33b, a channel tube 33d, and a cap 33e which form a treatment instrument channel 33A is provided in the insertion portion 21A. The channel hole 33b has a curving portion 33c corresponding to a tend-to-bend portion 14a provided in the treatment instrument insertion portion 11.

A proximal end side of the treatment instrument insertion portion 11 includes the projection amount detection mark 19. The raising table 35A may be provided in an over tube rather than in the endoscope.

According to the forward viewing endoscope configured as described above, the direction of rotation, around the major axis, of the treatment instrument insertion portion projecting from a distal surface of the frontward viewing endoscope and the amount of projection of the treatment instrument insertion portion can be matched with a preset state. Thus, the relationship between the joint in the distal bending portion of the treatment instrument insertion portion and the joint in the raising table can be preset to allow the inputting device to be operated with the relationship maximizing the movable range, the relationship for the direction requiring the maximum bending angle, and the like always maintained in the same state.

In the above-described embodiment, the presetting means corresponds to the tend-to-curve portion 14a, the curving portion 33c, and the projection amount detection mark 19. However, the presetting means is not limited to the tend-to-curve portion 14a, the curving portion 33c, and the projection amount detection mark 19. For example, another possible configuration may include a presetting member and a presetting portion shown in FIGS. 21 and 22 or a presetting portion shown in FIGS. 23 and 24.

Another example of the configuration of the presetting means will be described with reference to FIGS. 21 and 22.

Figure 21:
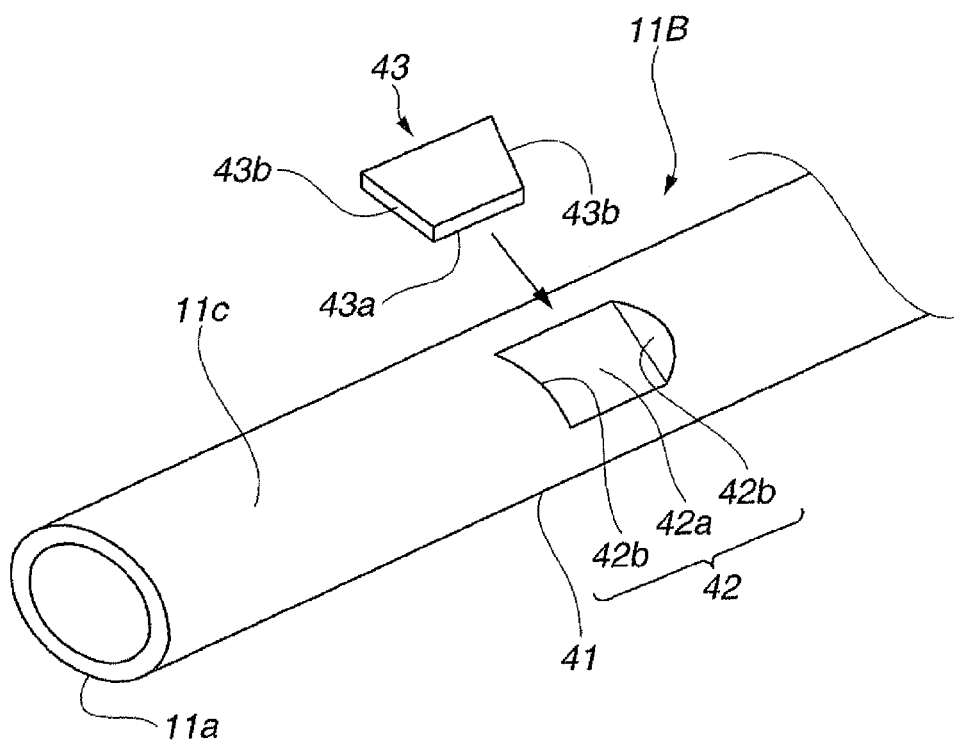

As shown in FIG. 21, a fit-in portion 42 that is a recess portion with a plane 42a and a tapered surface 42b is formed in, for example, a middle portion 41 of a treatment instrument insertion portion 11B of the treatment instrument 2. On the other hand, a presetting member 43 is provided, for example, at a predetermined position in the vicinity of the treatment instrument channel provided in the endoscope. The presetting member 43 includes an abutting surface 43a located in abutment with the plane 42a of the fit-in portion 42, and a slope 43b abutting the tapered surface 42b. The presetting member 43 is, for example, slidable in a direction of an arrow shown in FIG. 21 by means of an actuator (not shown in the drawings).

Figure 22:
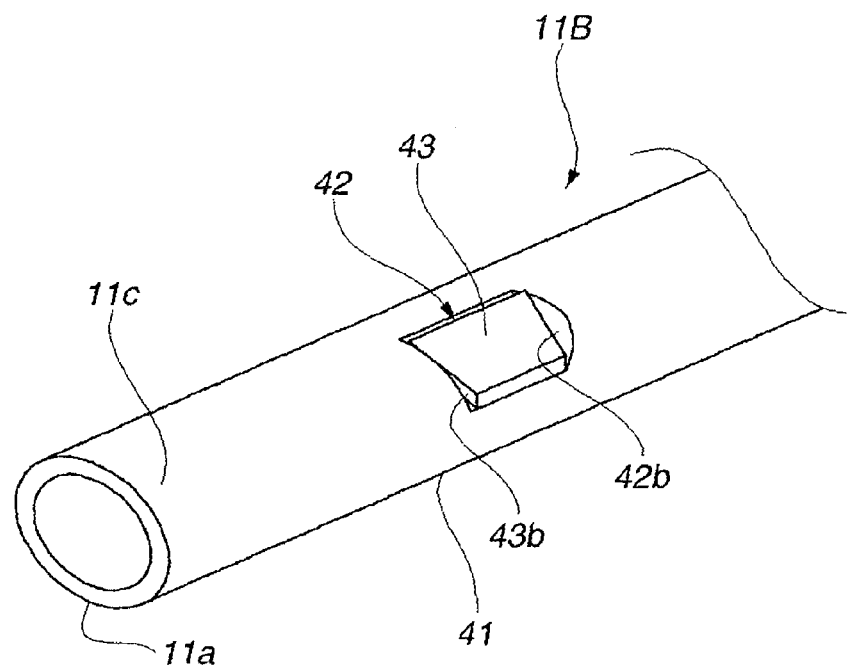

According to this configuration, as shown in FIG. 22, when the presetting member 43 is placed in the fit-in portion 42 so that the abutting surface 43a abuts the plane 42a, the major axis of the treatment instrument insertion portion 11B is placed at a preset position with respect to a longitudinal direction of a treatment instrument channel 33B. Furthermore, when the presetting member 43 is placed in the fit-in portion 42 so that the slope 43b abuts against the tapered surface 42b, the amount of projection of the treatment instrument insertion portion 11B from, for example, the endoscope is set to a preset value.

In this arrangement state, the treatment instrument insertion portion 11 is drawn out of the endoscope in a preset posture. In other words, with the presetting member 43 not placed in the fit-in portion 42, the treatment instrument insertion portion 11B is prevented from being drawn out of the endoscope in the preset posture. In this case, the operator or the staff member performs a readjustment operation such that the treatment instrument insertion portion 11B is drawn out of the endoscope in the preset posture.

Another example of the configuration of the presetting means will be described with reference to FIGS. 23 and 24.

Figure 23:
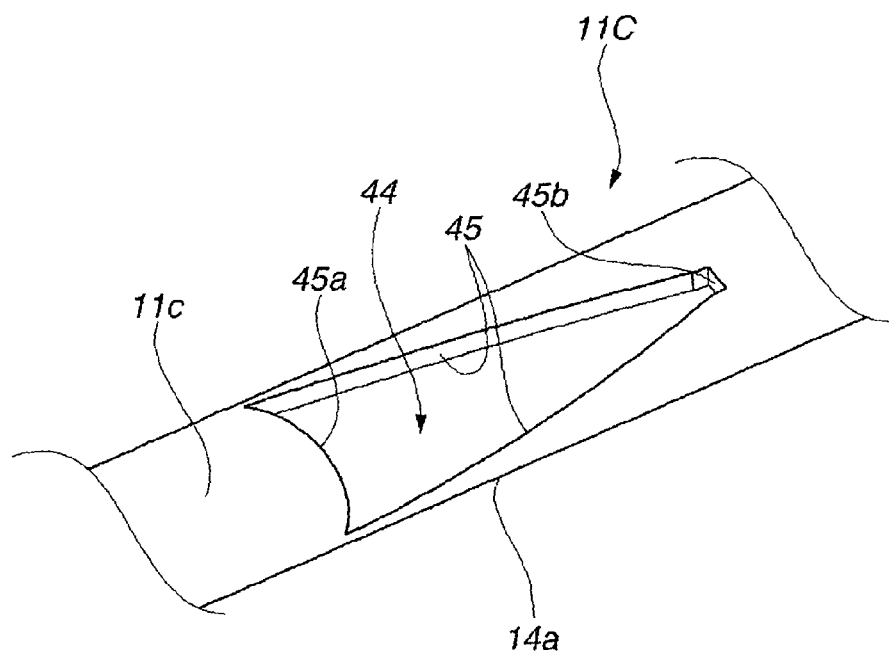

As shown in FIG. 23, a recess portion 44 shaped substantially like a rectangular parallelepiped is formed in a predetermined site of a side peripheral surface of, for example, the tend-to-curve portion 14a of a treatment instrument insertion portion 11C of the treatment instrument 2. The recess portion 44 includes a pair of slopes 45 at side portions thereof. The recess portion 44 includes a longer portion 45a located on a distal end side thereof and a projecting portion 45b located on a proximal end side thereof and forming an abutting surface. A width dimension of the projecting portion 45b is set such that a protruding portion 46 described below can be fitted in the projecting portion 45b. The protruding portion 46 shown in FIG. 24 is placed in the recess portion 44.

Figure 24:
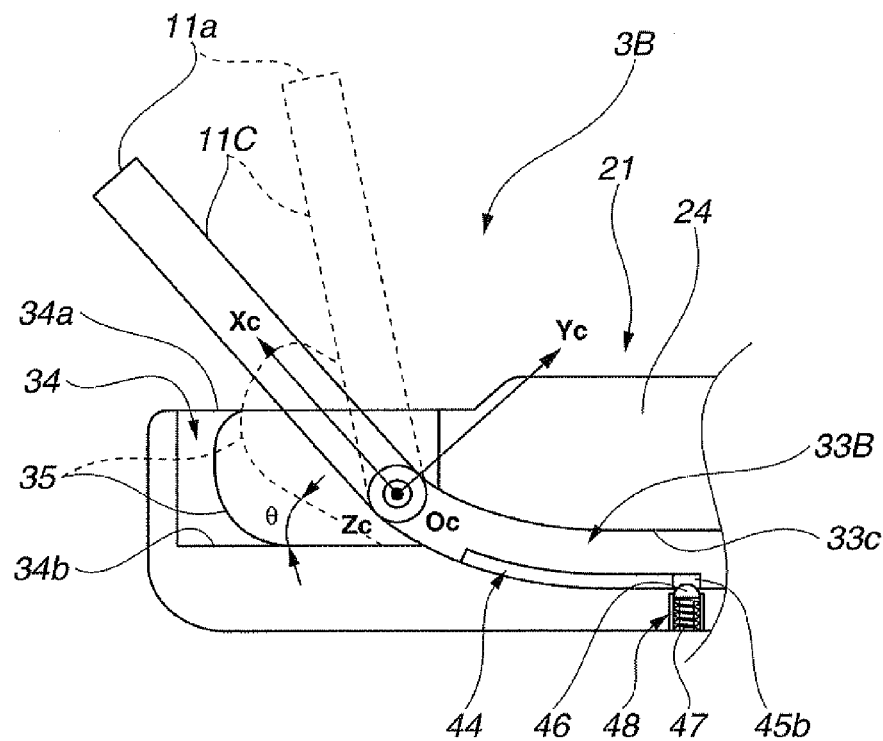

As shown in FIG. 24, the protruding portion 46 is configured to project and retract freely through a hole 48 by means of a spring 47 that is a biasing member. The protruding portion 46 is provided to lie on a proximal end side of the curving portion 33c of the treatment instrument channel 33B of an endoscope 3B.

According to this configuration, when a treatment instrument insertion portion 11C is inserted through the treatment instrument channel 33B, the following occurs because the protruding portion 46 is projected by a biasing force of the spring 47; when the distal end 11a of the treatment instrument insertion portion 11C reaches the curving portion 33c, the protruding portion 46 abuts against the distal end 11a to stop the insertion. Thus, the operator or the staff member determines that the distal end 11a of the treatment instrument insertion portion 11C has reached the curving portion 33c.

Then, the operator or the staff member operationally pushes in the treatment instrument insertion portion 11C by applying an amount of push-in force sufficient to resist the biasing force of the spring 47, to the treatment instrument insertion portion 11C. The protruding portion 46 is then pushed down to move the treatment instrument insertion portion 11C forward. When the distal bending portion 13 of the treatment instrument insertion portion 11C passes through the curving portion 33c, the distal end portion of the treatment instrument insertion portion 11C is displayed on the screen. The operator or the staff member thereafter continues the push-in operation.

At this time, if the treatment instrument insertion portion 11C is drawn out of the endoscope 3B in a state approximate to a preset one, the protruding portion 46 is placed in the recess portion 44 to reduce an insertion force amount. Thus, the operator or the staff member can determine that the treatment instrument insertion portion 11C has been inserted through the treatment instrument channel 33B in the preset state.

On the other hand, if the treatment instrument insertion portion 11C has been inserted through the treatment instrument channel 33 in a state different from the preset one, a draw-out amount increases, with the insertion force amount not reduced. In this case, the operator or the staff member determines that the treatment instrument insertion portion 11 has not been drawn out of the endoscope in the preset state, and performs the reinsertion operation.

With the protruding portion 46 placed in the recess portion 44, the protruding portion 46 abuts against the slope 45 to correct the misalignment of the treatment instrument insertion portion 11C with respect to the treatment instrument channel 33B in the major axis direction. Then, the protruding portion 46 is placed in the projecting portion 45b in abutment therewith. The operation of inserting the treatment instrument insertion portion 11C is thus completed.

At this time, the treatment instrument insertion portion 11C is drawn out through the opening 34a in the endoscope 3B in a preset posture because the rotating direction of the treatment instrument insertion portion 11C around the major axis and the projection amount thereof are preset.

The protruding portion 46 abuts against the slope 45 to slightly increase the insertion force amount. At this time, the operator or the staff member determines that the slight increase in insertion force amount is due to an increase in resistance resulting from the abutment of the protruding portion 46 against the slope 45. The operator or the staff member thus continues inserting the treatment instrument insertion portion into the treatment instrument channel.

Yet another configuration of the presetting means will be described with reference to FIGS. 25 and 26.

Figure 25:
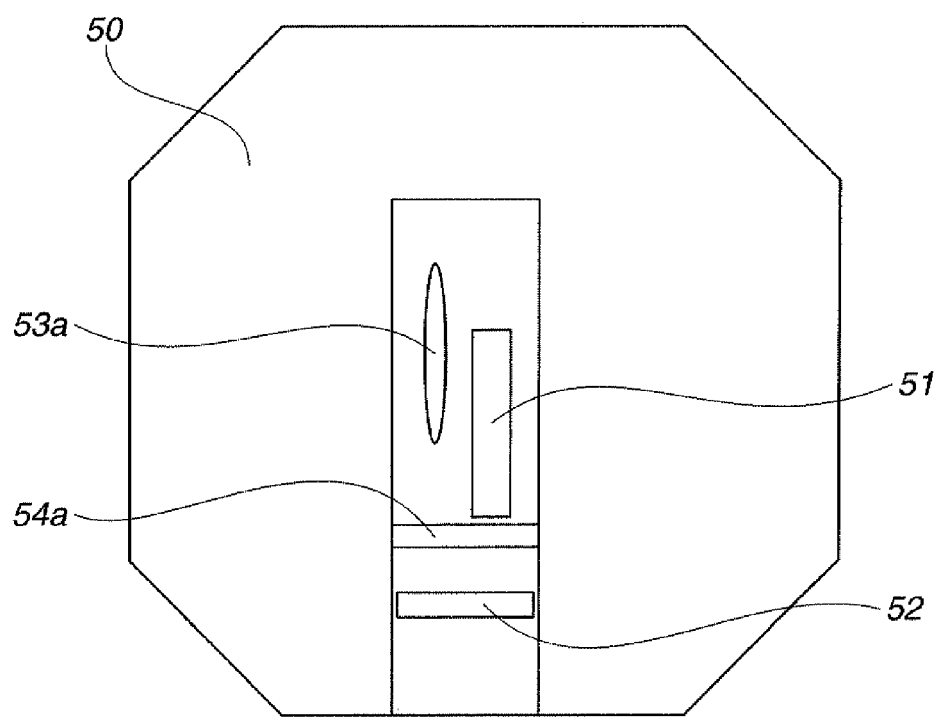

As shown in FIG. 25, in the present embodiment, an around-the-major-axis determination frame 51 and a projection amount determination frame 52 which are preset state determination frames are displayed on a screen 50 on which endoscopic images are displayed.

Here, reference numeral 53a denotes a first marking image. The first marking image 53a is a display image of an around-the-major-axis determination marking provided on the distal bending portion 13 of the treatment instrument insertion portion 11. Reference numeral 54a denotes a second marking image. The second marking image 54a is a display image of a projection amount determination marking provided on the distal bending portion 13 of the treatment instrument insertion portion 11. The projection amount determination marking is a peripheral marking formed around the major axis and having a predetermined width dimension.

Figure 26:
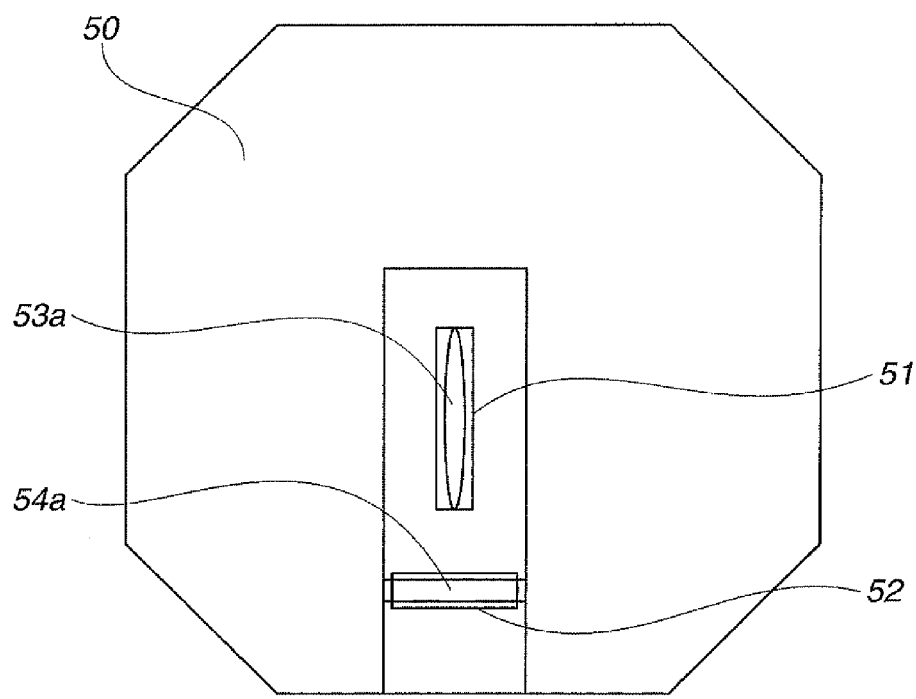

In this configuration, if the treatment instrument insertion portion 11 is drawn out of the endoscope in the preset posture, then as shown in FIG. 26, the first marking image 53a is placed in the around-the-major-axis determination frame 51. Furthermore, the second marking image 54a is placed in the projection amount determination frame 52.

That is, with the first marking image 53a placed in the around-the-major-axis determination frame 51 and the second marking image 54a placed in the projection amount determination frame 52, the treatment instrument insertion portion 11 is drawn out of the endoscope in the preset posture. In other words, when the marking images 53a and 54a are not placed in the corresponding determination frames 51 and 52 as shown in FIG. 25, the operator or the staff member can determine that the treatment instrument insertion portion 11 is not in the preset posture.

In this case, the operator or the staff member draws the treatment instrument insertion portion 11 out of the endoscope in the preset posture by performing an adjustment operation, for example, an operation of moving forward or backward or rotating the treatment instrument insertion portion 11. If the projection amount need not be preset, the operator or the staff member determines, visually or using a sensor, whether or not the second joint in the treatment instrument insertion portion projects further than the joint in the raising table.

Figure 27:
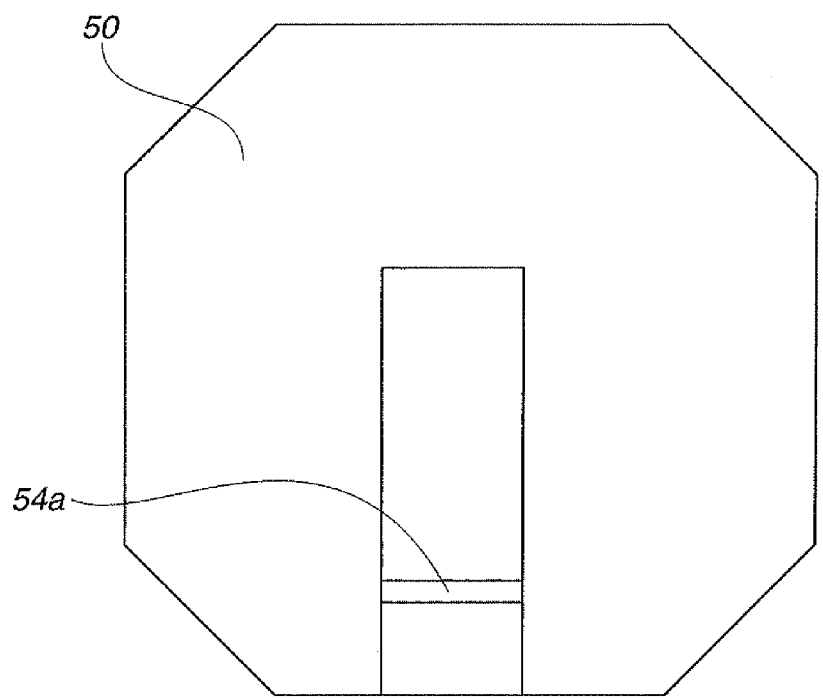

FIG. 27 shows a method of making the determination on the basis of the endoscopic image displayed on the screen 50 of the display device. As shown in FIG. 27, the operator or the staff member checks the screen for a marking image 54a of the projection amount determination marking to determine whether or not the joint 16 in the treatment instrument insertion portion 11 projects further than the joint 40 in the raising table 35. Thus, the projection amount determination marking is provided behind and at a predetermined distance from the distal bending portion 13 of the treatment instrument insertion portion 11.

Figure 28:
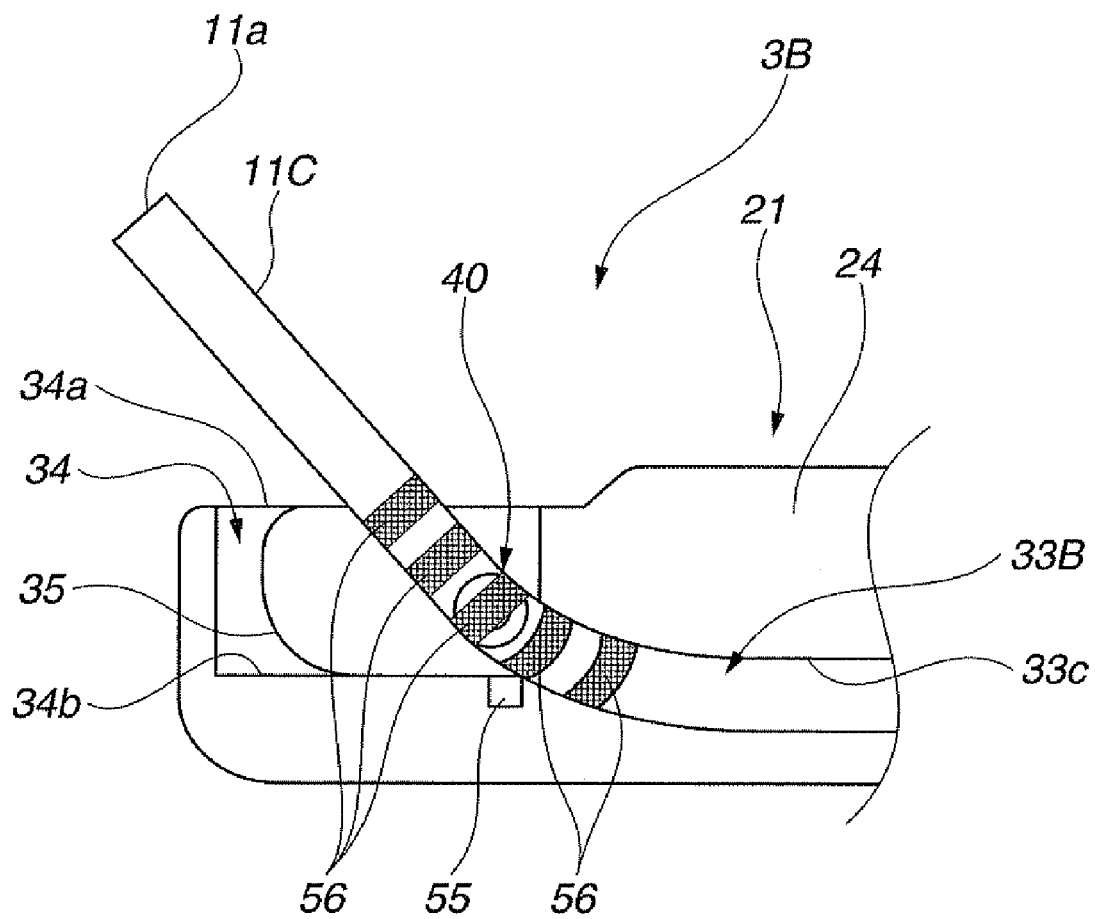

FIG. 28 shows an example of a configuration in which a sensor 55 is provided in the distal end portion 24. The sensor 55 is, for example, a magnetic sensor that detects, for example, a plurality of peripheral magnetic bodies 56 arranged around the major axis and behind the distal bending portion 13 of the treatment instrument insertion portion 11. When the sensor 55 detects the predetermined magnetic bodies 56, for example, the control portion 6a allows letters or the like indicating that the joints 15 and 16 in the treatment instrument insertion portion 11 project further than the joint 40 in the raising table 35, to be displayed in the screen (not shown in the drawings).

Upon thus determining that the joints in the treatment instrument insertion portion project further than the joint in the raising table, the operator or the staff member can control the operation of the joints 15, 16, and 40 to perform an operation of moving the distal end of the treatment instrument insertion portion.

A variation of the first embodiment of the present invention will be described with reference to FIG. 29.

Figure 29:
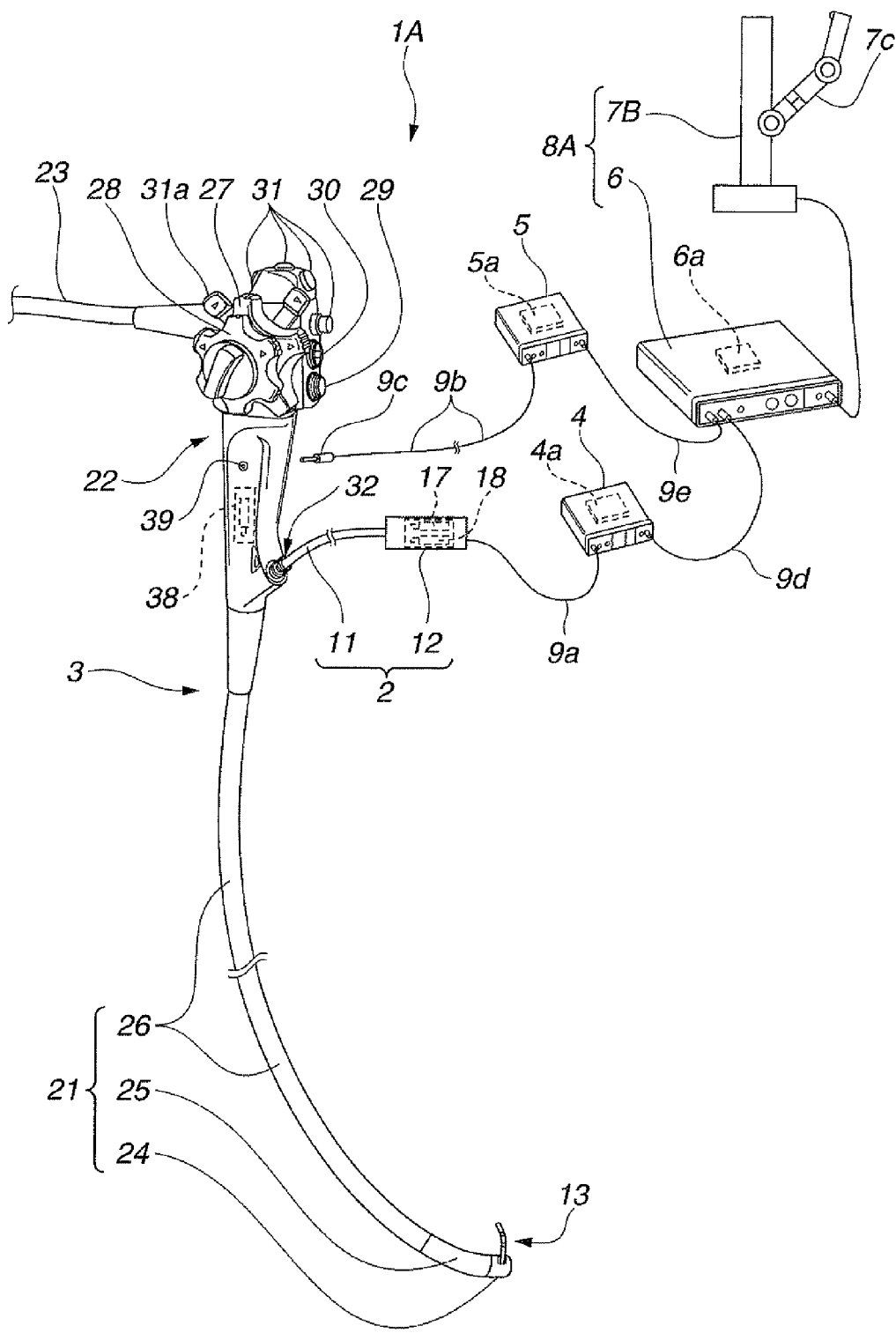
FIG. 29 is a diagram illustrating a variation of the medical apparatus.

A medical apparatus 1A shown in FIG. 29 includes an integrated medical device 8A. The integrated medical device 8A includes an inputting device 7B instead of the inputting device 7 that is the joy stick. The inputting device 713 includes an inputting portion 7c via which a target distal end position (X, Y, Z) and a target distal end posture (Roll, Pitch, Yaw) of the distal end 11a of the treatment instrument insertion portion 11 of the treatment instrument 2 are inputted. When the target distal end position (X, Y, Z) and the target distal end posture (Roll, Pitch, Yaw) are set via the inputting portion 7c, three values in each of the target distal end position (X, Y, Z) and the target distal end posture (Roll, Pitch, Yaw) are used as target values.

On the basis of inverse kinematics, the control portion 6a of the integrated controller 6 calculates target angles for the joint 40 in the raising table 35 and the joints 15 and 16 in the treatment instrument 2 which joints are in a preset positional and postural relationship with respect to the inputted target values as shown in FIG. 11. On the basis of the target angles, the control portion 6a controls the joints 15, 16, and 40.

Other configuration is similar to that in the first embodiment. The same members are denoted by the same reference numerals, and the description thereof is omitted.

Thus, the integrated medical device is composed of the integrated controller and the inputting device including the inputting portion via which the target distal end position and posture are inputted. Consequently, the operator can move the distal end of the treatment instrument insertion portion to any three-dimensional position within a movable range.

To increase a degree of freedom, the operator or the staff member can select a treatment instrument having a desired degree of freedom.

When the integrated medical device is combined with the inputting device including the inputting portion via which the target distal end position and posture are inputted, the operator can electrically drive the raising table of the endoscope and the bending portion of the treatment instrument by means of simpler operations to achieve wide ranges of the target distal end positions and postures.

A second embodiment of the medical apparatus will be described with reference to FIGS. 30 to 33.

Figure 30:
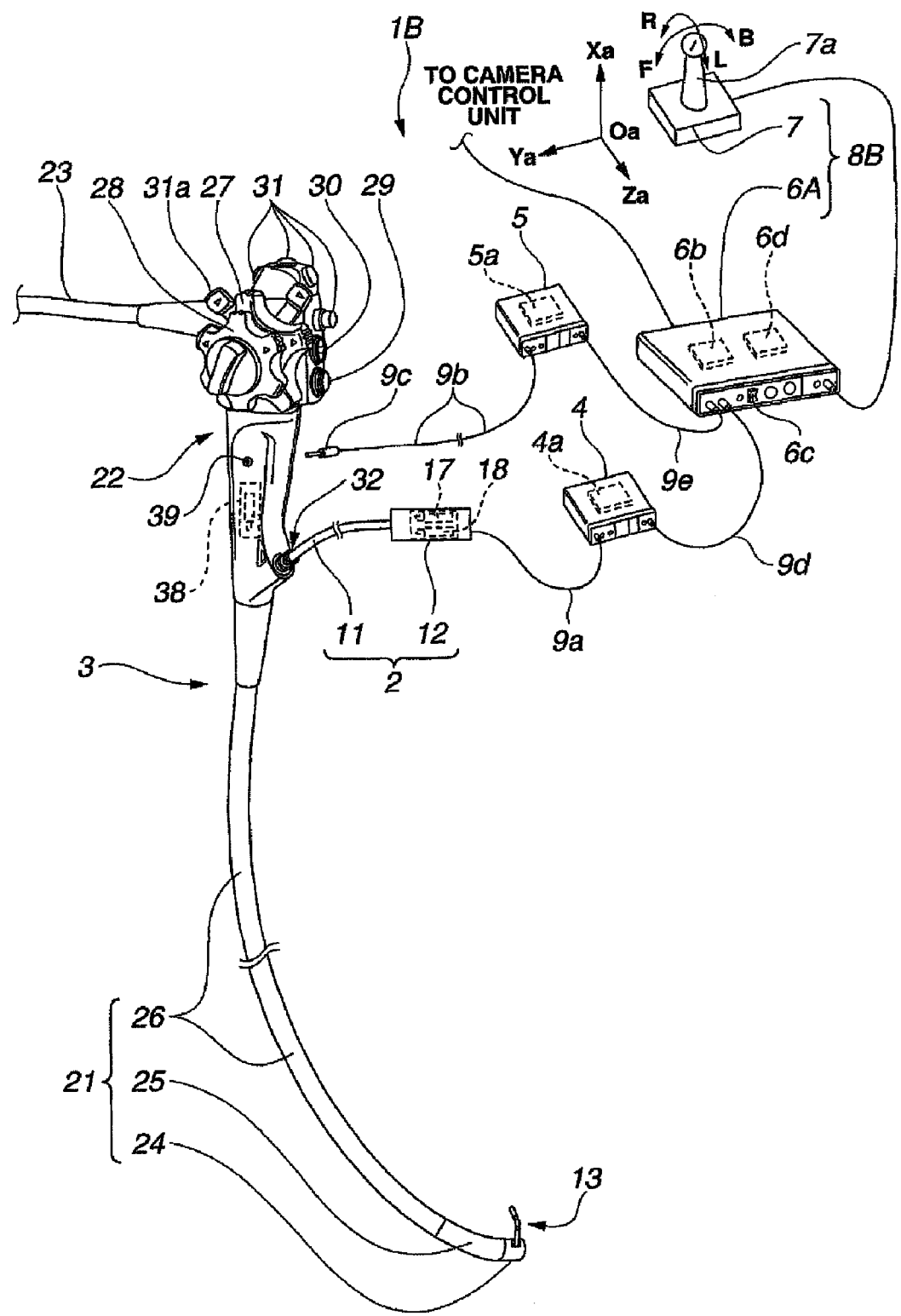
FIGS. 30 to 33 are diagrams relating to a second embodiment of the medical apparatus.

A medical apparatus 1B in FIG. 30 includes an integrated medical device 8B. The integrated medical device 8B includes an integrated controller 6A and an inputting device 7. The integrated controller 6A includes an image data acquiring portion 6b that is determination means, a measurement instruction switch 6c, and a control portion 6d. The image data acquiring portion 6b acquires image data of an endoscopic image generated by an image processing circuit provided in the camera control unit. When for example, the staff member operationally turns on the measurement instruction switch 6c, the control portion 6d of the integrated medical device 8B reads the marks provided on the distal bending portion 13 of the treatment instrument 2, from the image data acquired by the image data acquiring portion 6b. The control portion 6d thus acquires the postural and positional relationships of the treatment instrument insertion portion 11 drawn out of the endoscope 3.

Figure 31:
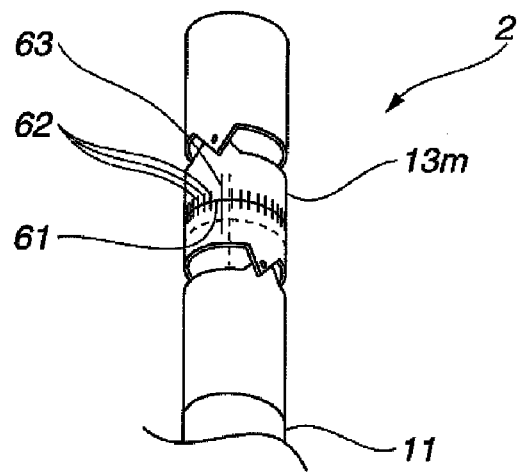

As shown in FIG. 31, a projection amount acquisition mark 61 and a plurality of rotation amount acquisition marks 62 are provided at predetermined positions on the central bending piece 13m, which forms the treatment instrument 2. The projection amount acquisition mark 61 is determination means for allowing the projection amount to be acquired. The plurality of rotation amount acquisition marks 62 are determination means for allowing the rotation amount in the major axis direction to be acquired.

The projection amount acquisition mark 61 is a peripheral line drawn in the center of the central bending piece 13m around the major axis. The projection amount acquisition mark is hereinafter referred to as the peripheral line 61. In contrast, the rotation amount acquisition marks 62 are a plurality of orthogonal lines that are orthogonal to the peripheral line 61 and parallel to the major axis. The rotation amount acquisition marks are hereinafter referred to as the orthogonal lines 62. A longer one of the plurality of orthogonal lines 62 is a reference line 63 showing the preset position.

For easier distinction, a color of the peripheral line 61 may be different from that of the orthogonal lines 62. Other configuration is similar to that in the first embodiment. The same members are denoted by the same reference numerals, and the description thereof is omitted.

An operation of the medical apparatus 1B configured as described above will be described.

First, the staff member constructs the medical apparatus 1B shown in FIG. 30.

Then, to diagnose or treat the bile duct, the pancreatic duct, or the like, the operator orally inserts the insertion portion 21 of the endoscope 3 until the insertion portion 21 reaches the duodenal bulb. At this time, observing an endoscopic image displayed on the screen of the display device (not shown in the drawings), the operator appropriately performs the operation of bending the bending portion 25 using the bending knobs 27 and 28, the operation of twisting the insertion portion 21, and the like. The operator thus draws out the distal end portion 24 to the vicinity of the opening in the papilla.

Then, the operator, for example, instructs the staff member to use the treatment instrument 2. In response to the instruction, the staff member inserts the treatment instrument insertion portion 11 of the treatment instrument 2 into the treatment instrument channel 33. The staff member then pushes in the treatment instrument insertion portion 11 to insert the treatment instrument insertion portion 11 through the channel tube 33d with the proximal end in communication with the treatment instrument insertion port 32. The staff member thereafter determines whether or not the projection amount detection mark 19 has reached the vicinity of the opening end of treatment instrument insertion port 32.

Figure 32:
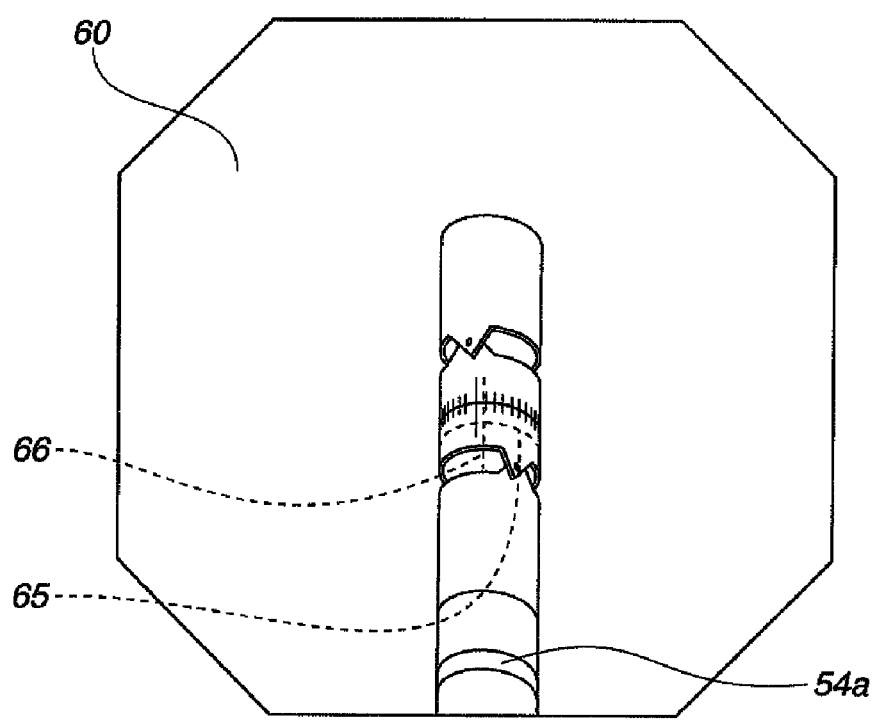
Figure 33:
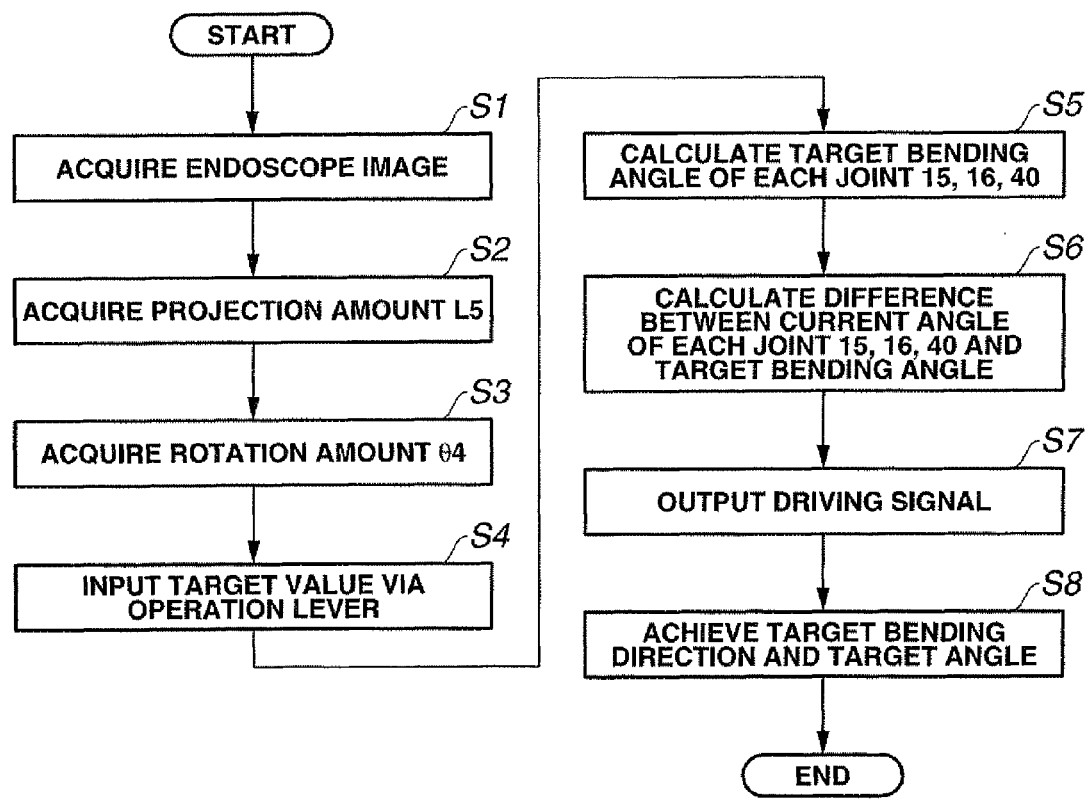

As the projection amount detection mark 19 approaches the opening end of the treatment instrument insertion port 32, the treatment instrument insertion portion 11 is drawn out through the opening 34a in the endoscope 3. Then, as shown in FIG. 32, the distal end 11a of the treatment instrument insertion portion 11 and a part of the distal bending portion 13 are displayed on a screen 60 of the display device.

Here, the operator determines whether or not the second joint 16 projects further than the raising joint 40, for example, on the basis of the marking image 54a of the projection amount determination marking in the endoscopic image.

Reference numeral 65 denotes a projection amount reference line (hereinafter referred to as a first reference line).

Reference numeral 66 denotes a major-axis-direction rotation amount reference line (hereinafter referred to as a second reference line).

Upon confirming the marking image 54a, the operator turns on the measurement instruction switch 6c. Then, as shown in step S1 in FIG. 33, the control portion 6d acquires an endoscopic image. The control portion 6d subsequently shifts to step S2 to acquire a projection amount L5 by which the joint 16 projects further than the joint 40, on the basis of a distance between the peripheral line 61 provided on the treatment instrument 2 and the first reference line 65 displayed on the endoscopic image from the endoscopic image. As shown in step S3, the control portion 6d further acquires a rotation amount θ4 in the major axis direction with respect to the preset state on the basis of a distance between the second reference line 66 displayed on the endoscopic image and the orthogonal line 62.

By executing these processes, the control portion 6d acquires data on the posture and position of the treatment instrument insertion portion 11 drawn out into the body through the opening 34a in the endoscope 3. During the data acquisition, the joints 15, 16, and 40 in the treatment instrument insertion portion 11 are not rotated.

Then, as shown in step S4, the operator operationally tilts the operation lever 7a to input the target values. The control portion 6d then shifts to step S5 to calculate target bending angles for the joints 15, 16, and 40 on the basis of the posture data acquired in steps S2 and S3 and the target values inputted via the operation lever 7a. Subsequently, as shown in step S6, the control portion calculates a difference between a current angle of each of the joints 15, 16, and 40 and the corresponding target bending angle calculated in step S5. The control portion shifts to step S7.

In step S7, the control portion 6d outputs driving control signals allowing the driving motor 38 and the driving actuators 17 and 18 to be driven. As a result, as shown in step S8, the raising table 35 and the distal bending portion 13 of the treatment instrument insertion portion 11 are driven to achieve target bending directions and the target angles. The driving is then stopped.

If in step S4, the operation lever 7a is operationally tilted to input the target values as shown in FIG. 14, the rotation angle θ1 of the joint 15 is the rotation angle $\theta1=(\beta/\beta max)\theta1max$, as is the case with the first embodiment. On the other hand, the rotation angles θ2 and θ3 of the joints 16 and 40 are determined with a rotation amount θ4 taken into account. The rotation angle $\theta2=\cos\theta4(\beta/\beta max)\theta2max$, and the rotation angle $\theta3=\sin\theta4(\beta/\beta3max)\theta3max$.

θ1max denotes the maximum bending angle of the raising joint 40. θ2max denotes the maximum bending angle of the joint 16. θ3max denotes the maximum bending angle of the joint 15.

A variation in projection amount L5, that is, a variation in length, may be used as a parameter for distributing the input of the operation lever 7a between the raising table 35 and the distal bending portion 13 of the treatment instrument 2 in the ratio of r1 to r2.

As described above, the projection amount acquisition mark and the rotation amount acquisition mark are provided on the bending piece forming the distal bending portion of the treatment instrument insertion portion forming the treatment instrument. Additionally, the integrated controller includes the image data acquiring portion that acquires image data generated by the image processing circuit. Furthermore, the integrated controller includes the control portion which acquires the posture data on the treatment instrument insertion portion from the image data and which generates the driving control signals allowing the driving motor and the driving actuators to be driven on the basis of the posture data and the current rotation angle and the target values of each of the joints. Thus, the target bending directions and target angles corresponding to the target values can be achieved by operationally tilting the operation lever to input the target values without the need to provide the presetting means composed of the tend-to-curve portion of the treatment instrument insertion portion of the treatment instrument and the curving portion of the treatment instrument channel of the endoscope.

This eliminates the need to provide the tend-to-curve portion in the treatment instrument insertion portion of the treatment instrument and the curving portion in the treatment instrument channel of the endoscope.

Since the rotation amount θ4 and the projection amount L5 are acquired from the endoscopic image, the correct posture and position data can be acquired only when the joints 15, 16, and 40 are in the preset state, that is, at 0°. Thus, the rotation amount θ4 and the projection amount L5 can always be measured, for example, by providing a rotation sensor directly acquiring the rotation amount θ4 on the basis of a pattern of energization or a variation in resistance value or a linear sensor directly acquiring the projection amount L5 on the basis of a difference in resistance value, the number of times that light has been turned on and off, or the number of times that energization has been turned on and off.

Furthermore, instead of the operation lever 7a, an inputting device 7B with the inputting portion 7c may be provided to allow the target distal end position (X, Y, Z) and the target distal end posture (Roll, Pitch, Yaw) to be set so that the target angles for the joints 15, 16, and 40 can be calculated on the basis of inverse kinematics to allow the joints 15, 16, and 40 to be controlled.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A medical apparatus comprising:
   a first medical device including:
      a treatment instrument insertion portion including:
         a bending portion, and
         a flexible tube portion provided proximally of the bending portion, the flexible tube portion including a tend-to-curve portion, and a recess portion provided at a predetermined site on a side peripheral surface of the tend-to-curve portion, the recess portion having a rectangular parallelepiped shape and a pair of slopes at side portions thereof,
      a first driving portion, which is electrically driven, for generating a driving force to bend the bending portion, and
      a first control device for drivingly controlling the first driving portion;
   a second medical device including:
      a treatment instrument channel through which the treatment instrument insertion portion of the first medical device can be inserted;
      a curving portion formed at a distal end of the treatment instrument channel;
      an external force applying portion for applying an external force to the treatment instrument insertion portion of the first medical device to move the treatment instrument insertion portion, a second driving portion, which is electrically driven, for generating a driving force to operate the external force applying portion, a second control device for drivingly controlling the second driving portion, and a protruding portion provided on a proximal end side of the curving portion, the protruding portion being operatively connected to a biasing member to protrude into and retract from the recess portion of the first medical device;

an integrated inputting device for instructing a distal end of the treatment instrument insertion portion to be moved to a target position or a target posture or in a target direction, in a configuration in which the external force of the external force applying portion provided in the second medical device can be applied to the treatment instrument insertion portion of the first medical device; and an integrated electrical control device, which is connected with the first control device of the first medical device and the second control device of the second medical device, for drivingly controlling the first control device and the second control device on the basis of an instruction from the integrated inputting device, to drivingly control the first driving portion and the second driving portion in conjunction to move the distal end of the treatment instrument insertion portion to the instructed target position or target posture or target direction, wherein the recess portion and the protruding portion are a presetting portion configured to preset the operation of the external force applying portion of the second medical device and the bending operation of the bending portion of the first medical device to a relationship for a predetermined position and a predetermined posture.

2. The medical apparatus according to claim 1, wherein the first medical device comprises a first inputting portion instructing the bending portion of the first medical device to be operationally bent to move the distal end of the treatment instrument insertion portion to the target position or the target posture or in the target direction, and the second medical device comprises a second inputting portion instructing the external force applying portion of the second medical device to be operated to move a distal end of the external force applying portion to a target position or a target posture or in a target direction.

3. The medical apparatus according to claim 1, further comprising:

an active treatment instrument that is the first medical device; and an endoscope that is the second medical device, the external force applying portion being an active bending applying mechanism provided in a distal end of the treatment instrument channel of the endoscope, and wherein the presetting portion presets amount of rotation of the treatment instrument insertion portion around a major axis of the treatment instrument insertion portion with respect to the active bending applying mechanism, and amount of projection of the treatment instrument insertion portion from the active bending applying mechanism.

4. The medical apparatus according to claim 1, wherein the integrated control device comprises:

in the configuration in which the external force of the external force applying portion of the second medical device can be applied to the treatment instrument insertion portion of the first medical device, a determination portion for determining the relationship for the position and the posture for the operation of the external force applying portion of the second medical device and the bending operation of the bending portion of the first medical device.

5. The medical apparatus according to claim 4, further comprising:

an active treatment instrument that is the first medical device; and an endoscope that is the second medical device, the external force applying portion being the active bending applying mechanism provided in a distal end of the treatment instrument channel of the endoscope, and wherein the determination portion determines the amount of rotation of the treatment instrument insertion portion around the major axis of the treatment instrument insertion portion with respect to the active bending applying mechanism, and the amount of projection of the insertion portion from the active bending applying mechanism.

6. The medical apparatus according to claim 1, wherein the first medical device comprises at least one joint for the first medical device for causing the bending portion provided to the treatment instrument insertion portion to rotate by a predetermined angle in one direction and another direction with respect to a predetermined axis.

7. The medical apparatus according to claim 1, wherein the second medical device comprises a rotatable joint for the second medical device for causing the external force applying portion to bend in a predetermined direction with respect to a predetermined axis.

8. The medical apparatus according to claim 1, wherein the presetting portion includes:

a projection amount detection mark provided to a flexible tube portion of the treatment instrument insertion portion of the first medical device, the projection amount detection mark presetting projection amounts of a tend-to-curve portion having a bending shape at a predetermined radius matching a bending direction of a joint for the second medical device of the second medical device, and of the treatment instrument insertion portion drawn out of the second medical device; and the curving portion having a bending shape matching the tend-to-curve portion of the treatment instrument insertion portion passed through the treatment instrument channel.

* * * * *